United States Patent
Zhou et al.

(10) Patent No.: US 10,807,242 B2
(45) Date of Patent: Oct. 20, 2020

(54) CONTROL MODES AND PROCESSES FOR POSITIONING OF A ROBOTIC MANIPULATOR

(71) Applicant: Verb Surgical Inc., Mountain View, CA (US)

(72) Inventors: Renbin Zhou, Wellington, FL (US); Haoran Yu, Sunnyvale, CA (US); Sina Nia Kosari, Fremont, CA (US); Omar J. Vakharia, Palo Alto, CA (US); Bernard Fai Kin Siu, San Jose, CA (US); Alex Kiturkes, Belmont, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 304 days.

(21) Appl. No.: 15/840,990

(22) Filed: Dec. 13, 2017

(65) Prior Publication Data
US 2019/0176334 A1    Jun. 13, 2019

(51) Int. Cl.
| | | |
|---|---|---|
| *A61B 34/30* | (2016.01) | |
| *B25J 9/16* | (2006.01) | |
| *A61B 90/00* | (2016.01) | |
| *A61B 34/37* | (2016.01) | |
| *A61B 90/50* | (2016.01) | |
| *A61B 90/57* | (2016.01) | |

(52) U.S. Cl.
CPC ............ *B25J 9/1679* (2013.01); *A61B 34/37* (2016.02); *A61B 90/03* (2016.02); *B25J 9/1689* (2013.01); *A61B 2090/5025* (2016.02); *A61B 2090/571* (2016.02); *G05B 2219/40117* (2013.01)

(58) Field of Classification Search
USPC .............................. 700/245–264; 606/1, 130
See application file for complete search history.

(56) References Cited

U.S. PATENT DOCUMENTS

| | | | | |
|---|---|---|---|---|
| 8,945,095 | B2 * | 2/2015 | Blumenkranz | B25J 15/0009 606/1 |
| 9,084,623 | B2 * | 7/2015 | Gomez | B25J 9/1656 |
| 2003/0191454 | A1 * | 10/2003 | Niemeyer | A61B 34/30 606/1 |
| 2006/0149147 | A1 * | 7/2006 | Yanof | A61B 17/3403 600/424 |
| 2011/0087238 | A1 * | 4/2011 | Wang | A61B 34/35 606/130 |
| 2013/0012821 | A1 * | 1/2013 | Lin | A61B 34/73 600/473 |

(Continued)

OTHER PUBLICATIONS

PCT Search Report and Written Opinion dated Mar. 1, 2018, for related PCT Appln. No. PCT/US17/066187 9 Pages.

(Continued)

*Primary Examiner* — Jonathan L Sample
(74) *Attorney, Agent, or Firm* — Womble Bond Dickinson (US) LLP

(57) ABSTRACT

A method for controlling a robotic arm in a robotic surgical system includes defining a reference plane at a predetermined reference location for a robotic arm, where the robotic arm includes a plurality of joints, and driving at least one of the plurality of joints to guide the robotic arm through a series of predetermined poses substantially constrained within the reference plane.

20 Claims, 15 Drawing Sheets

(56) References Cited

U.S. PATENT DOCUMENTS

| | | | | |
|---|---|---|---|---|
| 2013/0211588 A1* | 8/2013 | Diolaiti | .................. | B25J 9/1689 |
| | | | | 700/249 |
| 2013/0245375 A1* | 9/2013 | DiMaio | .................. | A61B 34/37 |
| | | | | 600/111 |
| 2014/0039517 A1* | 2/2014 | Bowling | ................ | A61B 34/10 |
| | | | | 606/130 |
| 2014/0316434 A1* | 10/2014 | Simaan | .................. | A61B 34/30 |
| | | | | 606/130 |
| 2017/0015001 A1* | 1/2017 | Faure-Vidal | ........... | B25J 9/1692 |
| 2017/0079731 A1* | 3/2017 | Griffiths | ................. | A61B 34/30 |
| 2017/0172674 A1* | 6/2017 | Hanuschik | ............. | A61B 34/35 |
| 2018/0080841 A1* | 3/2018 | Cordoba | .................. | B25J 18/04 |

OTHER PUBLICATIONS

International Preliminary Report on Patentability for International Application No. PCT/US2017/066187 dated Jun. 25, 2020, 8 pages.
Examination Report for Australian Application No. 2017442655 dated Jul. 9, 2020, 4 pages.
Extended European Search Report for European Application No. 17934498.1 dated Aug. 5, 2020, 7 pages.

* cited by examiner

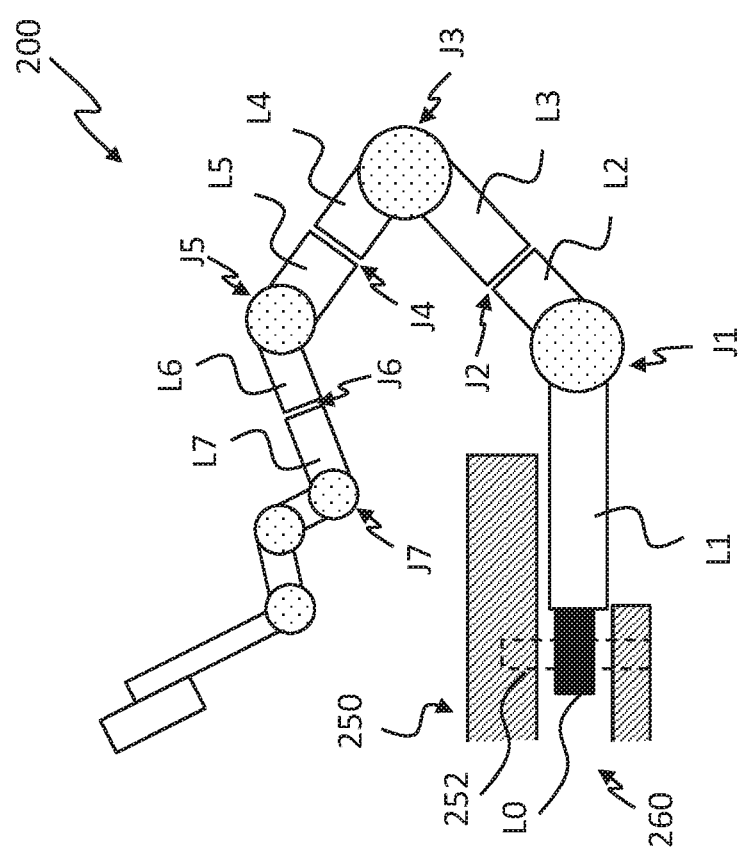

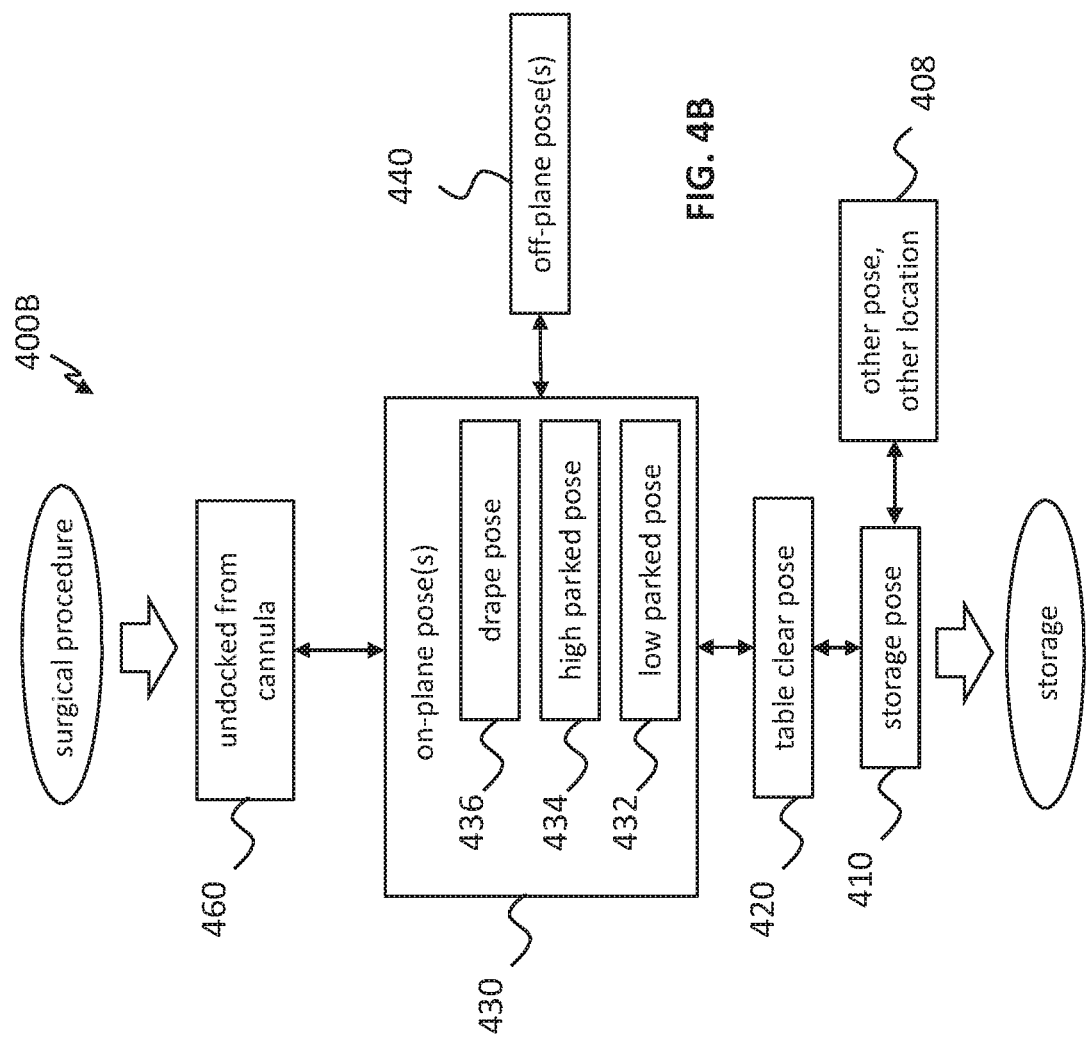

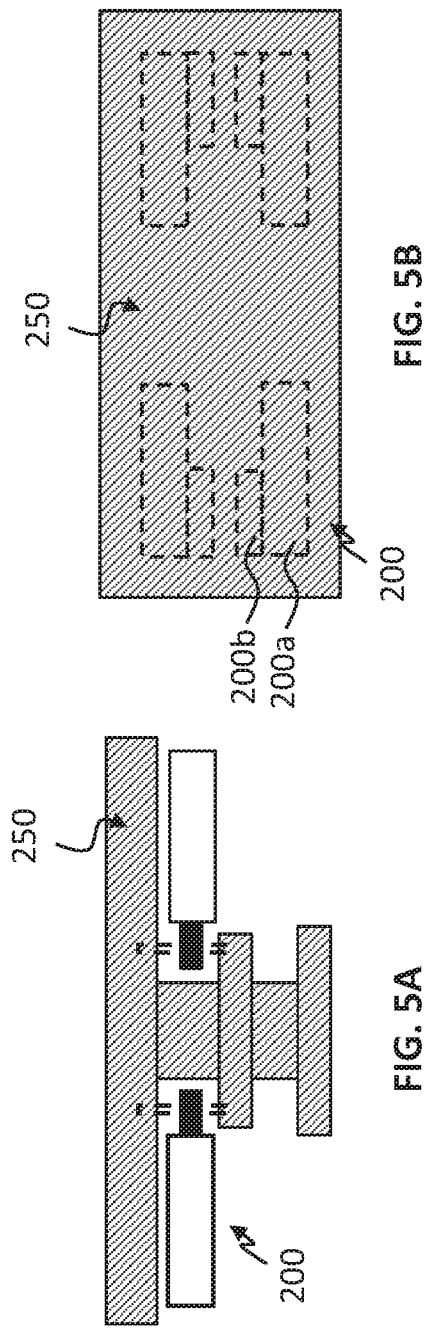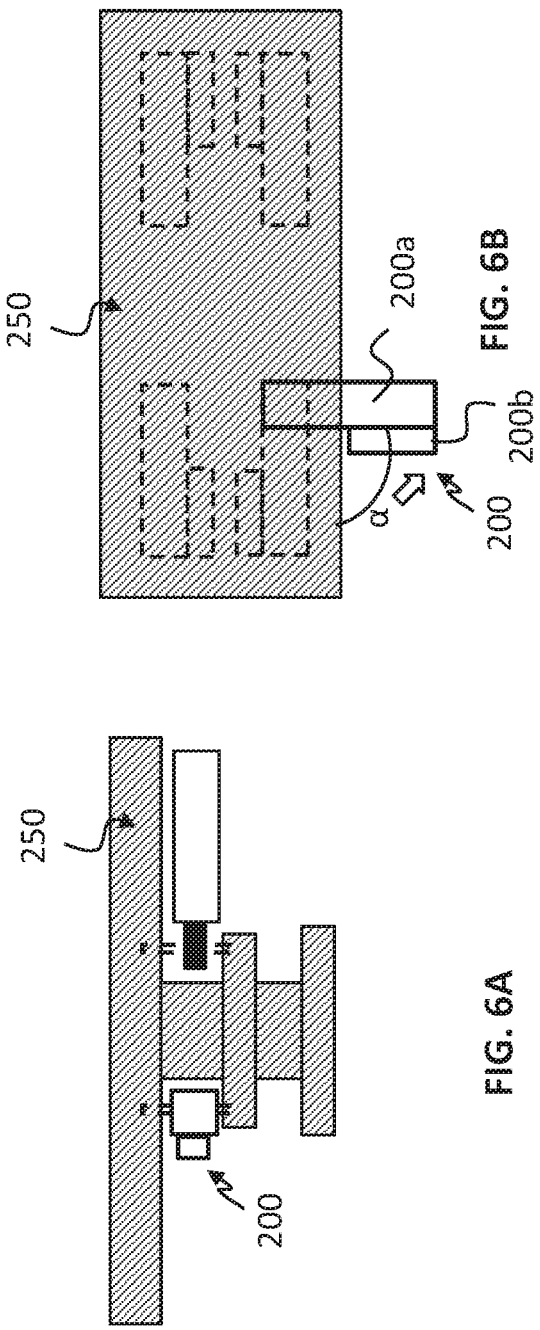

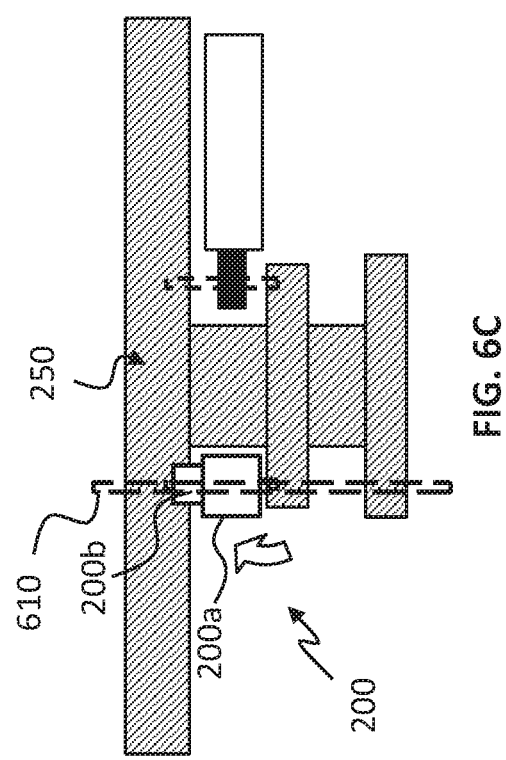

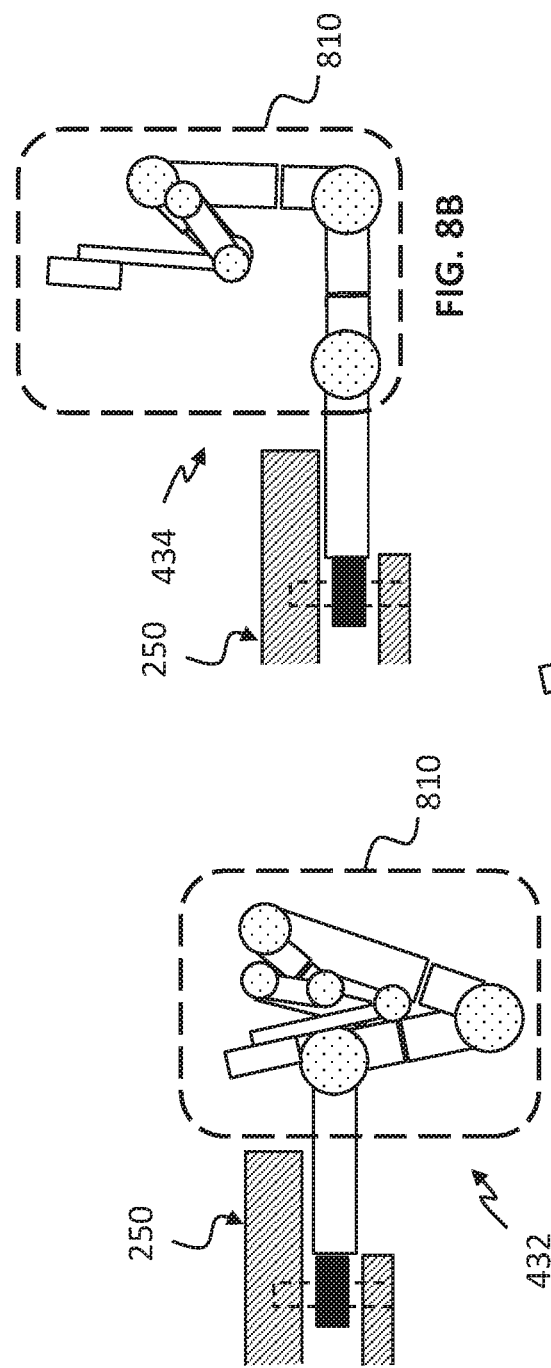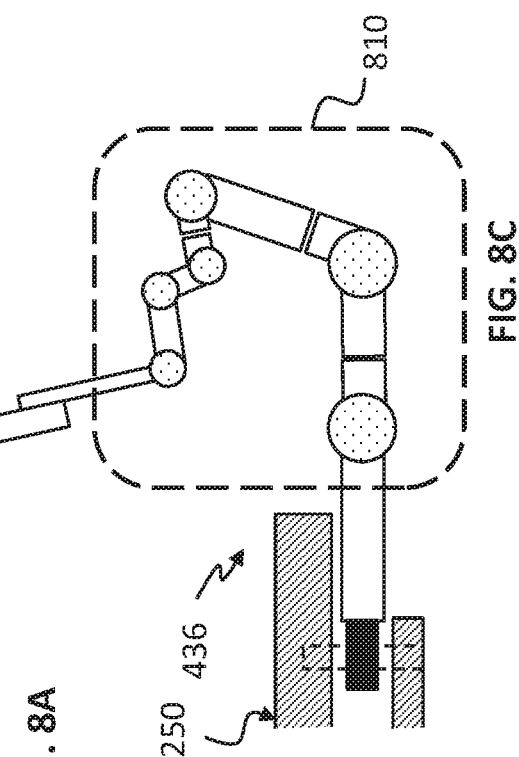

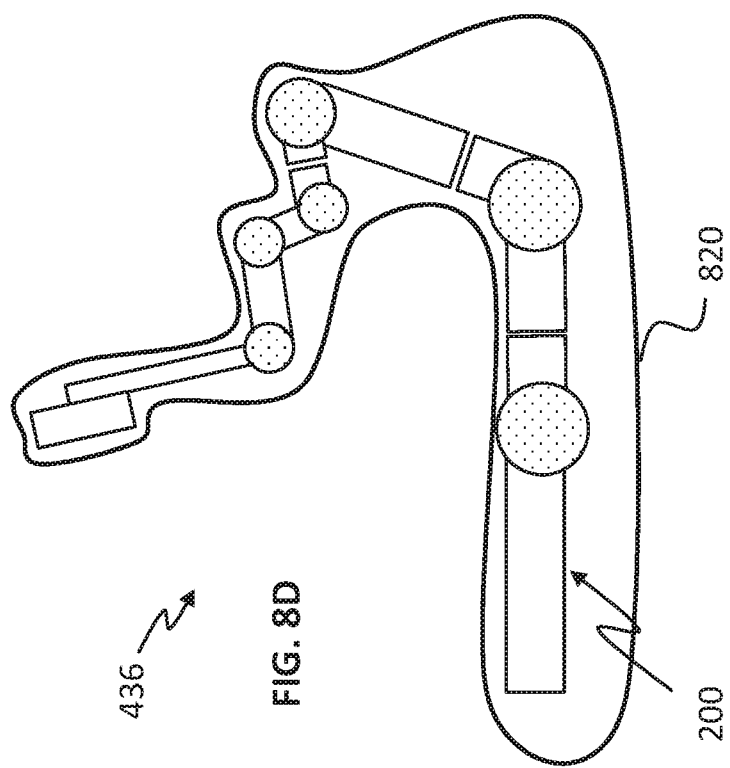

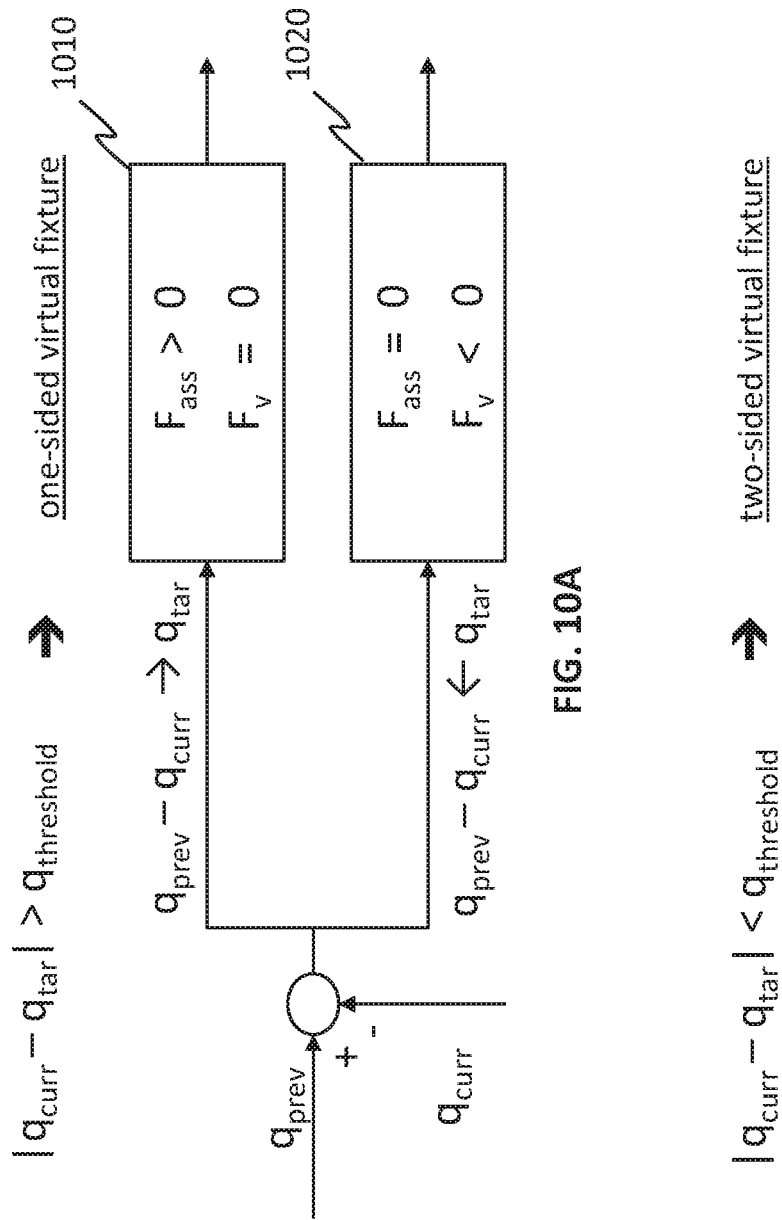

CONTROL MODES AND PROCESSES FOR POSITIONING OF A ROBOTIC MANIPULATOR

TECHNICAL FIELD

This invention relates generally to the field of robotic surgical systems, and more specifically to systems and methods for controlling a robotic surgical system.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more instruments (e.g., one or more tools, at least one camera, etc.) through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating instruments based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. Such user interface devices may enable a surgeon or other user to operate the robotic system from a remote location (e.g., in teleoperation).

Setup of a robotic MIS system (e.g., before a surgical procedure) can be a complicated process, since such a system includes many components that require coordination for proper setup. Similarly, "teardown", or restoration of a robotic MIS system (e.g., after a surgical procedure) to a storage or transport mode, can be complicated for similar reasons. Thus, it is desirable to have control modes and processes for assisting and simplifying pre-operative setup and post-operative teardown of the robotic surgical system.

SUMMARY

Generally, in some variations, a method for controlling a robotic arm in a robotic surgical system includes defining a reference plane at a predetermined reference location for a robotic arm, wherein the robotic arm includes a plurality of joints, and driving (e.g., with one or more actuators) at least one of the plurality of joints to guide the robotic arm through a series of predetermined poses substantially constrained within the reference plane. The series of predetermined poses may include, for example, an ordered sequence of progressively unfolded predetermined poses (e.g., for pre-operative positioning of the robotic arm, or for transitioning the robotic arm from a storage pose) or progressively folded predetermined poses (e.g., for post-operative positioning of the robotic arm, or for transitioning the robotic arm to a storage pose). As another example, the series of predetermined poses may implemented in intra-operative positioning of the robotic arm.

In some variations, the method may include guiding the robotic arm to the reference plane from a storage pose. In these variations, the series of predetermined poses may include an ordered sequence of progressively unfolded predetermined poses. In yet other variations, the method may additionally or alternatively include guiding the robotic arm to the reference plane to transition to a storage pose. In these variations, the series of predetermined poses may include an ordered sequence of progressively folded predetermined poses. In driving at least one of the plurality of joints to guide the robotic arm through an ordered sequence of predetermined poses, at least one joint may be driven forward and/or backward through at least a portion of the ordered sequence.

Different variations of guidance for the robotic arm may be provided. In some variations, when driving at least one of the plurality of joints to guide the robotic arm within the reference plane, at least one of the plurality of joints may be driven in response to an external force on the robotic arm, such as a user-applied force when a user manually manipulates the robotic arm. For example, at least one of the plurality of joints may be driven to apply a gravity compensation torque and/or a friction compensation torque. In some variations, when driving at least one of the plurality of joints to guide the robotic arm within the reference plane, at least one of the plurality of joints may be driven to enforce a task space virtual fixture defined at the reference plane, to substantially constrain the robotic arm (or selected points thereof) within the reference plane. Other processes for guidance include enforcing a joint space virtual fixture, in that at least one of the plurality of joints may be driven to enforce a uni-directional joint space virtual fixture on the at least one joint, and/or generating a virtual attractive force at the at least one joint in a joint space virtual fixture, to bias the robotic arm toward the reference plane and substantially constrain the robotic arm (or selected points thereof) within the reference plane. Furthermore, the method may, in some variations, include driving at least one joint in the robotic arm according to a predetermined trajectory through the series of predetermined poses.

Generally, in some variations, a robotic surgical system includes at least one robotic arm including a plurality of joints, and a processor configured to control movement of the robotic arm before or after a surgical procedure, by defining a reference plane at a predetermined reference location and driving at least one of the plurality of joints to guide the robotic arm through a series of predetermined poses substantially constrained within the reference plane. Similar to the methods described above, in some variations, the series may include an ordered sequence of progressively unfolded predetermined poses (e.g., for a pre-operative process), while in some variations, the series may include an ordered sequence of progressively folded predetermined poses (e.g., for a post-operative process).

In these variations, the processor may be configured to drive at least one of the plurality of joints of the robotic arm to guide the robotic arm in any of various manners. For example, the processor may be configured to drive (e.g., with one or more actuators) at least one of the joints in accordance with a task space virtual fixture and/or a joint space virtual fixture. As another example, the processor may be configured to drive at least one joint in response to an external force on the robotic arm (e.g., applied by a user who is manually manipulating the robotic arm), and/or provide at least one of gravity compensation and friction compensation to at least one joint to assist movement of the robotic arm. As yet another example, the processor may be configured to drive at least one joint according to a predetermined trajectory through the series of predetermined poses.

BRIEF DESCRIPTION OF THE DRAWINGS

FIG. 2A is a schematic illustration of another exemplary variation of an instrument driver on a robotic arm manipulator, coupled to a patient table.

FIG. 4B is a flowchart of an exemplary workflow after a surgical procedure for a robotic surgical system.

FIGS. 5A and 5B are illustrative schematic side and top views, respectively, of robotic arms in an exemplary variation of a storage pose under a patient table.

FIGS. 6A and 6B are illustrative schematic side and top views, respectively, of a robotic arm moving to an exemplary variation of a table clear pose at an exemplary reference location. FIG. 6C is an illustrative schematic side view of a robotic arm rotating onto an exemplary reference plane.

FIGS. 8A-8C are exemplary variations of different on-plane poses within an exemplary reference plane. FIG. 8D is a schematic illustration of a drape pose of the robotic arm covered with a sterile drape.

FIGS. 10A and 10B are diagrams illustrating an exemplary variation of a control system implementing a combination of virtual fixtures for a robotic arm.

DETAILED DESCRIPTION

Figure 1A:
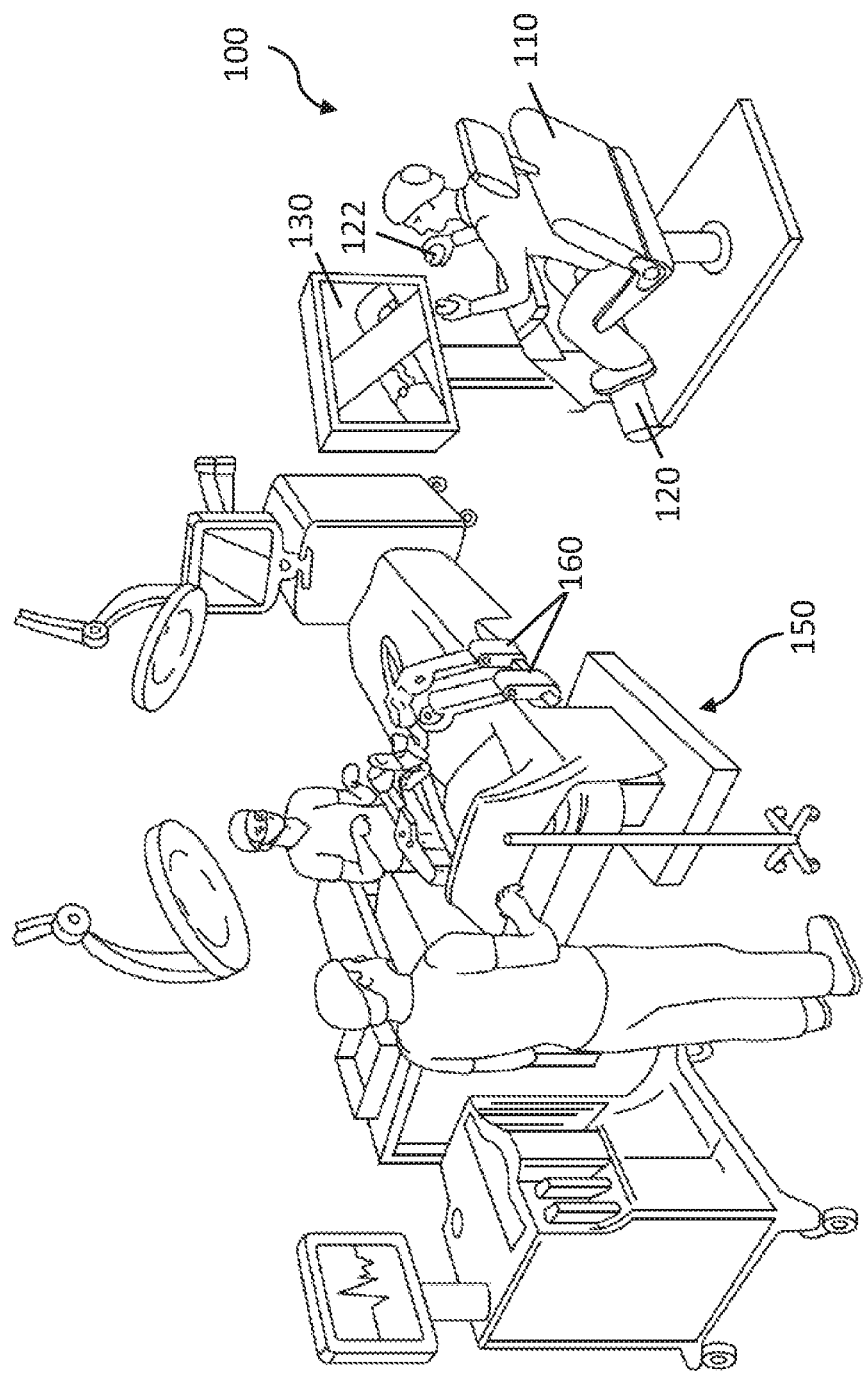
FIG. 1A depicts an example of an operating room arrangement with a robotic surgical system and a surgeon console.
Figure 1B:
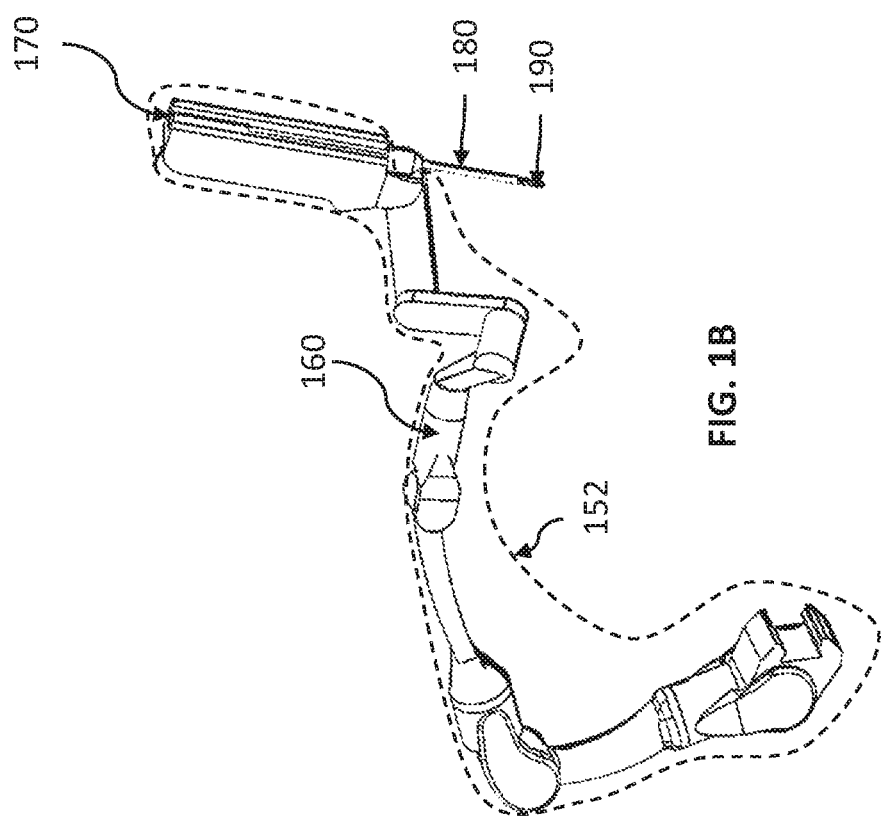
FIG. 1B is a schematic illustration of one exemplary variation of an instrument driver on a robotic arm manipulator.

Non-limiting examples of various aspects and variations of the invention are described herein and illustrated in the accompanying drawings.
Robotic Surgical System Overview Generally, as shown in FIG. 1A, a robotic system 150 may include one or more robotic arms 160 located at a surgical platform (e.g., table, bed, cart, etc.), where end effectors or surgical tools are attached to the distal ends of the robotic arms 160 for executing a surgical procedure. For example, a robotic system 150 may include, as shown in the exemplary schematic of FIG. 1B, at least one robotic arm 160 coupled to a surgical platform, and an instrument driver 170 generally attached to a distal end of the robotic arm 160. A cannula 180 coupled to the end of the instrument driver 170 may receive and guide a surgical instrument 190 (e.g., end effector, camera, etc.). Furthermore, the robotic arm 160 may include a plurality of links that are actuated so as to position and orient the instrument driver 170, which actuates the surgical instrument 190. A sterile drape 152 or other sterile barrier may be interposed between non-sterile components (e.g., robotic arm 160 and instrument driver 170) and sterile components (e.g., cannula 180) to help maintain a sterile field for the patient (e.g., to protect against contamination from non-sterile components).

A user (such as a surgeon or other operator) may use the user console 100 to remotely manipulate the robotic arms 160 and/or surgical instruments (e.g., tele-operation). The user console 100 may be located in the same procedure room as the robotic system 150, as shown in FIG. 1A. In other embodiments, the user console 100 may be located in an adjacent or nearby room, or tele-operated from a remote location in a different building, city, or country, etc.

In one example, the user console 100 comprises a seat 110, foot-operated controls 120, one or more handheld user interface devices 122, and at least one user display 130 configured to display, for example, a view of the surgical site inside a patient. For example, as shown in the exemplary user console shown in FIG. 1C, a user located in the seat 110 and viewing the user display 130 may manipulate the foot-operated controls 120 and/or handheld user interface devices to remotely control the robotic arms 160 and/or surgical instruments. The user console may, in some variations, further include one or more arm supports 140 (e.g., a left-side arm support and a right-side arm support) which may generally be configured to provide support to the arms of the user located in the seat 110 during a surgical procedure. For example, the arm supports 140 may provide an ergonomic resting surface for the user's arms, thereby reducing fatigue. Other exemplary functions of the arm supports 140 are described elsewhere herein.

During an exemplary procedure or surgery, the patient is prepped and draped in a sterile fashion, and anesthesia is achieved. Initial access to the surgical site may be performed (e.g., with an incision in the patient). Once access is completed, initial positioning and/or preparation of the robotic system may be performed (e.g., as further described herein). During the surgical procedure, a surgeon or other user in the user console 100 may utilize the foot-operated controls 120 and/or user interface devices 122 to manipulate various end effectors and/or imaging systems to perform the procedure. Manual assistance may also be provided at the procedure table by sterile-gowned personnel, who may perform tasks including but not limited to retracting organs, or performing manual repositioning or tool exchange involving one or more robotic arms 160. Non-sterile personnel may also be present to assist the surgeon at the user console 100. When the procedure or surgery is completed, the robotic system 150 and/or user console 100 may be configured or set in a state to facilitate one or more post-operative procedures, including but not limited to robotic system 150 cleaning and/or sterilization, and/or healthcare record entry or printout, whether electronic or hard copy, such as via the user console 100.

In FIG. 1A, the robotic arms 160 are shown with a table-mounted system, but in other embodiments, the robotic arms may be mounted in a cart, ceiling or sidewall, or other suitable support surface. The communication between the robotic system 150, the user console 100, and any other displays may be via wired and/or wireless connection(s). Any wired connections may be optionally built into the floor and/or walls or ceiling. The communication between the user console 100 and the robotic system 150 may be wired and/or wireless, and may be proprietary and/or performed using any of a variety of data communication protocols. In still other variations, the user console 100 does not include an integrated display 130, but may provide a video output that can be connected to output to one or more generic displays, including remote displays accessible via the internet or network. The video output or feed may also be encrypted to ensure privacy and all or portions of the video output may be saved to a server or electronic healthcare record system.

In other examples, additional user consoles 100 may be provided, for example to control additional surgical instruments, and/or to take control of one or more surgical instruments at a primary user console. This will permit, for example, a surgeon to take over or illustrate a technique during a surgical procedure with medical students and physicians-in-training, or to assist during complex surgeries requiring multiple surgeons acting simultaneously or in a coordinated manner.

Table and Robotic Arm

Generally, as described above, one or more robotic arms in a robotic surgical system may be located at a surgical platform, such as a table, bed, cart, etc. For example, as shown in FIG. 2A, one exemplary variation of a robotic arm 200 may be coupled to a table 250 via a coupling arrangement 260. The coupling arrangement 260 may enable the robotic arm 200 to pivot or move laterally relative to the surface of the table 250 (in and out of the page, as shown in the orientation of FIG. 2A). The coupling arrangement 260 may, for example, include a pin 252 coupled to the table 250, and a coupling link L0 rotatably coupled to the pin 252 so as to form a pivot joint or pin joint. The coupling arrangement 260 may further include an actuator (e.g., motor and geartrain) configured to enable powered movement of the robotic arm 200 relative to the table 250 via an actuatable joint around pin 252. The coupling arrangement 260 may include at least one position sensor, such as an encoder coupled to an actuator in the coupling arrangement 260 or another suitable angle sensor, configured to measure the position or orientation of the robotic arm 200 relative to the table 250. Furthermore, in some variations, one or more brakes may be included in the coupling arrangement 260 so as to selectively arrest relative movement of the robotic arm 200 relative to the table 250.

Although the robotic arm 200 is primarily described herein as being coupled to the table 250 via a pivotable coupling arrangement, it should be understood that in other variations, the robotic arm 200 may additionally or alternatively be coupled to the patient table with other kinds of mechanisms, including but not limited to mechanisms facilitating longitudinal or lateral movement, such as tracks, pin-in-slot, or other suitable mechanisms.

The robotic arm 200 may include multiple links (arm segments), and multiple actuated joint modules that drive or regulate relative movement between adjacent links. Each joint module may include an actuator, a geartrain (e.g., harmonic drive), encoder, torque sensor, and/or other suitable actuator, transmission, etc. for moving arm links, and/or suitable sensors for detecting positional and/or torque feedback. Such feedback may, for example, be used to provide input into control schemes operating the robotic arm. One or more joint modules may include one or more brakes (e.g., drum brake) that may arrest relative movement of adjacent links and/or hold or lock relative positions of adjacent links, such as for holding the robotic arm in a particular pose or configuration.

For example, as shown in FIG. 2A, a robotic arm 200 may include at least seven joint modules actuating joints J1-J7 in the robotic arm 200, where J1-J7 includes pivot joints and/or roll joints. J1 may enable relative pivot movement between a first link L1 and a second link L2. J2 may enable relative roll movement between the second link L2 and a third link L3. J3 may enable relative pivot movement between the third link L3 and a fourth link L4. J4 may enable relative roll movement between the fourth link L4 and a fifth link L5. J5 may enable relative pivot movement between the fifth link L5 and a sixth link L6. J6 may enable relative roll movement between the sixth link L6 and a seventh link L7. J7 may enable relative pivot movement between the seventh link L7 and an eighth link L8. For example, in some variations, the combination of pivot joints J1, J3, J5, and J7 and roll joints J2, J4, and J6 may enable a robotic arm that has at least seven degrees of freedom and is movable into various poses including those described herein. However, it should be understood that the robotic arm shown in FIG. 2 is exemplary only, and the methods described herein may be used to control any suitable kind of robotic arm.

Figure 2B:
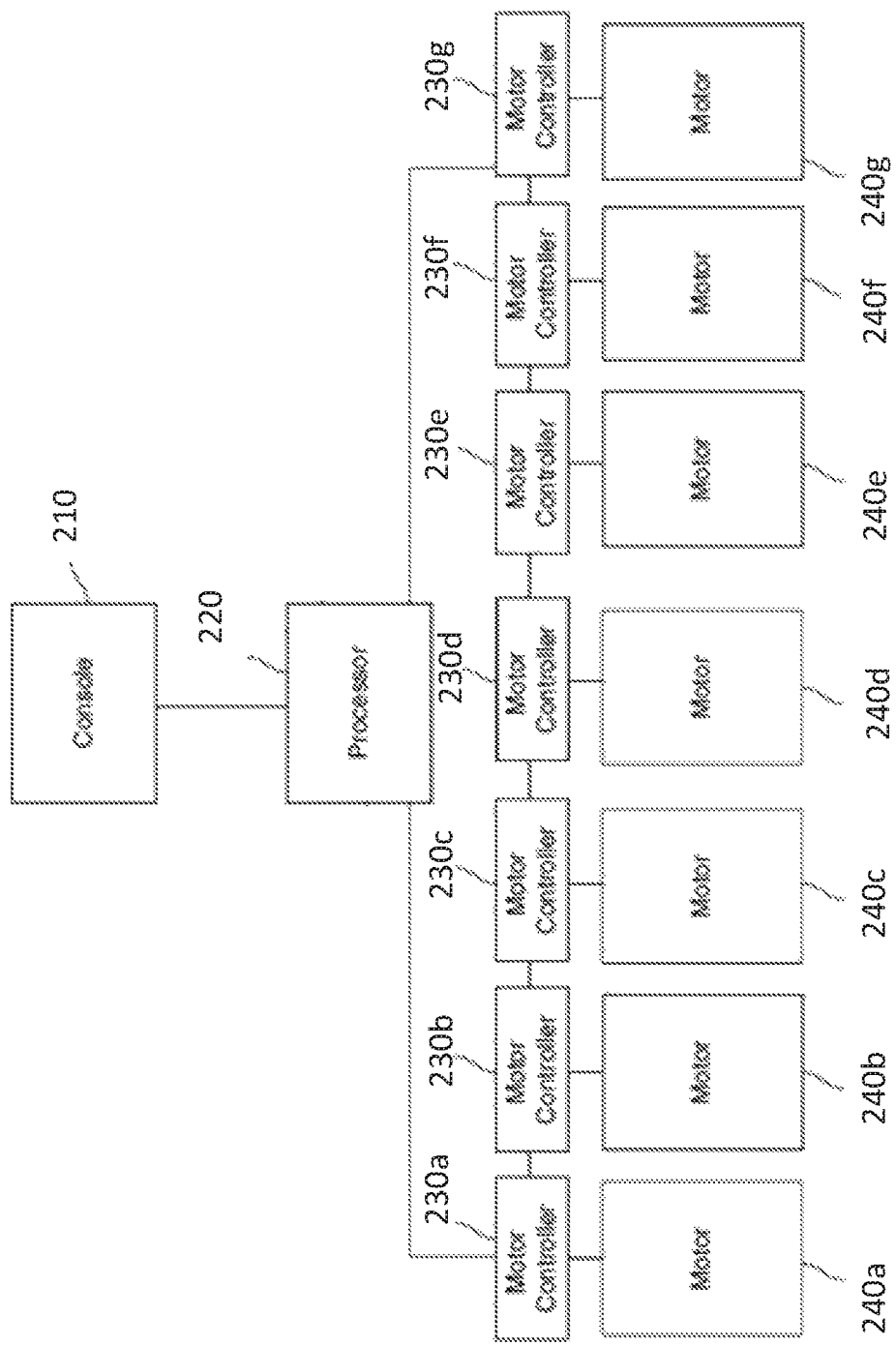
FIG. 2B is an overview schematic of an exemplary control system setup for controlling actuation of the joint modules of one exemplary variation of a robotic arm.

In some variations, the robotic arm may be controlled by a control system that governs actions of the robotic arm. The control system may control multiple robotic arms, if the robotic-assisted surgical system includes more than one robotic arm. For example, as shown in FIG. 2B, the control system may include one or more processors 220 (e.g., a microprocessor, microcontroller, application-specific integrated circuit, field programmable gate array, and/or other logic circuitry). The processor 220, which may be physically located on the robotic arm itself, in a cart-carried unit, or other suitable structure, may be communicatively linked to a user console 210 (e.g., a user interface). The processor 220 may, for example, be configured to execute instructions for performing any combination of aspects of the methods described herein. The control system may further include a set of multiple motor controllers (e.g., 230a-230g), each of which is communicatively coupled to the processor 220 and dedicated to control and operate at least one actuator in a respective joint module in the robotic arm (e.g., 240a-240g).

In some variations, one or more various control modes may be used to operate the robotic arm. For example, the robotic arm may be operated in a gravity compensation control mode, in which the robotic arm holds itself in a particular pose without drifting downward due to gravity. In gravity compensation mode, the control system determines the gravity force acting on at least a portion of the links in the robotic arm. In response, the control system actuates at least one joint module to counteract the determined gravity force such that the robotic arm can maintain the current pose. To determine the gravity force, for example, the controller may perform calculations based on measured joint angles between adjacent links, known kinematic and/or dynamic properties of the robotic arm and instrument driver, and/or known characteristics of the actuator (e.g., gear ratio, motor torque constants), detected force(s) on joints, etc. Furthermore, the robotic arm may include at least one accelerometer or other suitable sensor(s) configured to determine the direction of the applied gravitational force on the arm. Based on these calculations, the controller may algorithmically determine what force at each joint module is needed to compensate for gravity force acting on that joint module. For example, the controller may utilize a forward kinematic algorithm, an inverse dynamic algorithm, or any suitable algorithm. The controller may then generate a set of commands to provide the actuators in the joint modules with an appropriate level of current which holds the robotic arm in the same pose. The gravity compensation mode may, for example, be used alone or in combination with other control modes (e.g., friction compensation mode described below) in various situations, such as during pre-operative and/or post-operative processes as described herein.

As another example, the robotic arm may be operated in a friction compensation mode, or active back-drive mode. For example, in some situations, a user may wish to directly manipulate (e.g., pull or push) one or more of the arm links to arrange the robotic arm in a particular pose. These actions back-drive the actuators of the robotic arm. However, due to friction caused by mechanical aspects such as high gear ratios in the joint modules, in some variations, the user must apply a significant amount of force in order to overcome the friction and successfully move the robotic arm. To address this, the friction compensation mode enables the robotic arm to assist a user in moving at least a portion of the robotic arm, by actively back-driving appropriate joint modules in the direction needed to achieve the pose desired by the user. As a result, the user may manually manipulate the robotic arm with less perceived friction or with an apparent "lightweight" feel. In some variations, the controller may also incorporate pre-defined parameters (e.g., duration of a force) to help distinguish between movement that is accidental (e.g., a brief bump of an arm) and a sudden intended shift in arm position, then correct or reestablish arm position in the event a movement is determined to be accidental.

In friction compensation mode, the control system may determine the presence and direction of a user-applied force acting on at least one joint module (either directly or indirectly as the result of force on one or more arm links) to back-drive the actuator in that joint module. In response, the control system may actuate the joint module in the same direction as the user-applied force to help the user overcome static or dynamic friction. To determine the presence, magnitude, and direction of the user-applied force, the control system may monitor the velocity and/or position of the joint modules or robotic links (e.g., with force or torque sensors, accelerometers, etc.). Additionally, when in friction compensation mode, the control system may send a dithering current signal to (e.g., a sine wave or square wave centered at zero, with frequency of about 0.5 Hz-1.0 Hz or other suitable frequency, and with amplitude within the friction band in both directions) one or more joint modules, such that the joint modules are primed to nearly, but not quite, overcome friction in either actuator direction. In response to determining the presence and direction of user-applied force, the control system may then generate a set of commands to provide the actuators in the joint modules with appropriate level of current to more responsively overcome friction. The friction compensation mode may, for example, be used alone or in combination with other modes (e.g., gravity compensation mode) in various situations, such as during pre-operative and/or post-operative processes as described herein.

Method for Guiding Robotic Arm

Figure 3A:
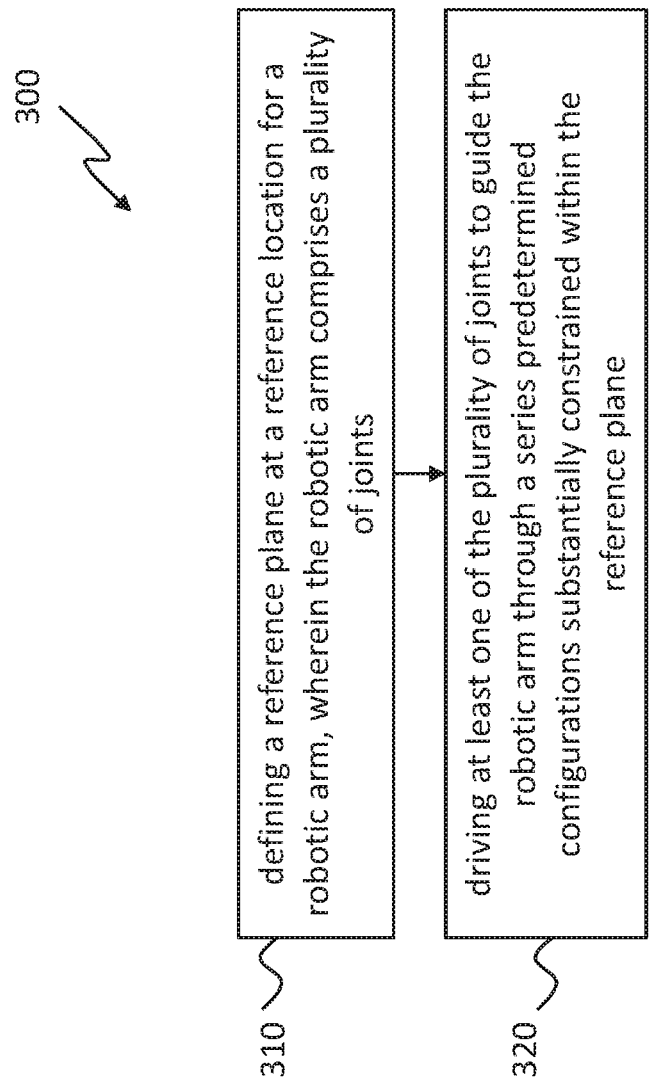
FIG. 3A is a flowchart of an exemplary variation of a method for controlling a robotic arm in a robotic surgical system.

Generally, methods for guiding movement of a robotic arm are provided herein. For example, as shown in FIG. 3A, a method 300 for guiding movement of a robotic arm in a robotic surgical system may include defining a reference plane at the reference location for a robotic arm 310, where the robotic arm includes a plurality of joints, and driving (e.g., with one or more actuators) at least one of the plurality of joints 320 to guide the robotic arm through a series of predetermined poses substantially constrained within the reference plane. For example, as described below, the robotic arm may be guided by driving at least one of the plurality of joints in task space and/or in joint space. In some variations, driving at least one of the plurality of joints 320 may be in response to manual manipulations of the robotic arm, so as to assist a user in repositioning or reposing the robotic arm, as further described herein.

In some variations, the method 300 may assist in positioning the robotic arm in pre-operative and/or post-operative processes (e.g., "setup" and "teardown" procedures) before and after a surgical procedure, respectively. For example, a pre-operative process may transition the robotic arm from a storage pose, and a post-operative process may transition the robotic arm to a storage pose. In some variations, the method 300 may assist in positioning the robotic arm intra-operatively, during a surgical procedure. In one aspect, through control modes as further described herein, the method may facilitate movement among robotic arm poses in a consistent and predictable manner that is compatible with clinical workflow. In another aspect, user-defined and/or predetermined robotic arm poses may be linked or tied together through a virtual construct such as the reference plane that organizes and/or constrains movement of the robotic arm in a controlled manner. For example, the reference plane may be configured as a virtual fixture, as further described herein, that generally limits movement of the robotic arm using predefined rules, thereby increasing the predictability of how the robotic arm moves. Such predictability and/or constraint of the robotic arm may, for example, help reduce inadvertent collisions between neighboring robotic arms, self-collision between different links of a robotic arm, collisions between a robotic arm and the patient table and/or other nearby obstacles, etc. In some variations, the reference plane may be predetermined (e.g., a precalculated or predefined location in space that is stored in memory and received for use during pre-operative and/or post-operative processes). For example, a particular reference plane (e.g., relative to the patient table) may be a general location suitable for a varied range of situations, or may be associated with a particular surgery type, a particular patient type, a particular user (e.g., based on surgeon preferences), particular equipment such as type of patient table, etc. In other variations, the reference plane may be stored in memory (e.g., relative to a current position of one or more links of the robotic arm) for use during the pre-operative and/or post-operative process.

The method 300 may guide movement of the robotic arm among various poses, including user-desired poses and/or predetermined poses, thereby assisting the user (e.g., surgeon or surgical assistant) to manipulate the robotic arm in a flexible manner suitable for various situations. In some variations, the method 300 may provide such benefits through a convenient interface for users to manipulate the robotic arm before, during, and/or after a surgical procedure.

In some variations, general pre-operative and post-operative workflows may incorporate multiple robotic arm poses, or poses, that are related to transitioning between a storage context and a surgical procedure context. Some of the robotic arm poses may be on-plane within a reference plane, where the reference plane may help guide the robotic arm to move between the on-plane robotic arm poses. In some variations, an "on-plane" pose may be a pose in which the entire robotic arm, or at least key points on the robotic arm (e.g., certain joints of the robotic arm) lie substantially within a reference plane. Additionally, some of the robotic arm poses may be off-plane outside of the reference plane, where the reference plane may provide a reference point or general "home" location to which the robotic arm may return to continue in the pre-operative or post-operative workflows.

As described in further detail below, in some variations, the robotic arm may be guided at least in part via a user input device, such as remotely commanded with a handheld communication device that is configured to send and/or receive signals from the robotic arm (and/or table adapter coupling the robotic arm to the patient table), or generally locally with buttons or other input mechanisms on the patient table, robotic arm, etc. In other variations, the robotic arm may additionally or alternatively be guided at least in part with an external force directly on the robotic arm, such as forces imparted by a user manually manipulating the robotic arm directly. In these variations, at least one of the plurality of joints in the robotic arm may be driven to effect commanded movement of the robotic arm and/or to provide assistance to the user's manipulations of the robotic arm, in order to guide the robotic arm through predetermined poses.

Although the methods described herein are primarily discussed with reference to a single robotic arm, it should be understood that in variations in which the robotic surgical system includes multiple robotic arms, at least some of the multiple robotic arms may be controlled through the pre-operative and/or post-operative workflows simultaneously in similar manners. In other variations, at least some of the multiple robotic arms may be controlled through the pre-operative and/or post-operative workflows sequentially (e.g., one at a time). Furthermore, at least some of the robotic arm may be controlled through respective intra-operative workflows simultaneously or independently.

Furthermore, although the methods described herein include references to a robotic arm coupled to a patient table, it should be understood that in some variations, the methods may be performed with respect to a robotic arm that is mounted to any suitable support surface (e.g., cart, ceiling, sidewall, etc.).

Guidance in Task Space

Generally, in some variations and in at least some circumstances, the robotic arm may be controlled by generating and applying a task space virtual fixture to the robotic arm. The task space virtual fixture may be, for example, a straight or curved line, planar or curved surface, volume, or other construct in three-dimensional space (e.g., defined in Cartesian space or other suitable spatial coordinates). For example, the control system may generally limit motion of one or more control points on the robotic arm (e.g., any suitable virtual point on the robotic arm) to locations on or within the virtual fixture. The task space virtual fixture may be predetermined (e.g., a precalculated or predefined location in space that is stored in memory and received for use during pre-operative and/or post-operative processes). For example, a particular task space virtual fixture may be a general virtual fixture suitable for a varied range of situations, or may be associated with a particular surgery type, a particular patient type, a particular user (e.g., based on surgeon preferences), particular equipment such as type of patient table, etc. In some variations, the task space virtual fixture may be stored in memory (e.g., relative to a current position of one or more links of the robotic arm) for use during the pre-operative, intra-operative, and/or post-operative process.

In some variations, as described herein, a virtual fixture may be defined on a reference plane for the robotic arm, such that the movement of the robotic arm (or selected points thereon) is substantially constrained to the reference plane. For example, a user may manually manipulate and position the robotic arm with the actuated assistance provided by gravity compensation and/or friction compensation control modes. The virtual fixture may generally permit such user-manipulated motion of the robotic arm within the reference plane, while substantially preventing or discouraging motion outside of the reference plane. For example, motion outside of the reference plane may be resisted by delivering a set of one or more resistance joint torques opposing one or more force components that are perpendicular to the reference plane (any force component that tends to cause a portion of the robotic arm to move outside of the reference plane). The control system may drive one or more of the joints in the robotic arm to deliver the resistance joint torque in accordance with the virtual fixture.

Desired virtual force F for the resistance joint torques $\tau$ may be calculated as Cartesian forces (e.g., X-Y-Z components) according to Equation (1), as a sum of a virtual spring force and a virtual damping force:

$$F = K^* \Delta x + D^* v_x \quad (1)$$

where F=Cartesian component forces (3×1 vector), K=spring constants (3×3 diagonal matrix), $\Delta x$=penetration depth (3×1 vector), D=damping ratio (3×3 diagonal matrix), and $v_x$=velocities (3×1 vector). In some variations, the virtual force F may omit the virtual spring force (the component with the spring constants K) or the virtual damping force (the component with the damping ratio D). The virtual force F may be used to determine resistance joint torques $\tau$ across the joints J of the robotic arm according to Equation (2):

$$\tau = J^{T*}[F, O]^T \quad (2)$$

where $\tau$=resistance joint torques (n number of joints×1 vector), F=forces (3×1 vector), and O=zeroes (3×1 vector). Each resistance joint torque may be effected or imposed by actuation of a respective joint module in the robotic arm, such that relevant joints of the robotic arm are driven to oppose attempted out-of-plane movement of at least a portion of the robotic arm. Although dimensions of the matrices in Equations (1) and (2) are configured for Cartesian forces, it should be understood that in other variations, the matrices may be any suitable dimensions for expressing force and torque in other kinds of coordinate systems (e.g., spherical).

In some variations, the robotic arm (or selected points thereon) may be moved outside of the reference plane (virtual fixture) if sufficient external force applied to the robotic arm exceeds a threshold value. For example, the virtual force F described above may saturate at threshold values, or have maximum predetermined values, such that if a user attempts to move the robotic arm with enough force to overcome the maximum virtual force F, at least a portion of the robotic arm may be forced outside of the reference plane. The maximum or saturation value of the virtual force F may be adjustable as a system setting (e.g., system mode). In some examples, the maximum value of the virtual force F may be variable and based on other conditions, such as type of surgical procedure to be performed, speed of movement of the robotic arm, mode or pose of the robotic arm (e.g., associated with a particular step of the setup and/or teardown process), etc. Once the robotic arm is outside of the reference plane, the movement outside of the reference plane of the robotic arm may, in some variations, be actively assisted with gravity compensation and/or friction compensation. The robotic arm may furthermore be restored onto the reference plane and into the constraints of the virtual fixture via, for example, guidance in joint space as described below.

Although guidance in task space is primarily described above with respect to a planar virtual fixture, it should be understood that other virtual fixture shapes (e.g., straight or curved line, curved surfaces, three-dimensional volumes, etc.) may be similarly implemented.

Guidance in Joint Space

Generally, in some variations and in at least some circumstances, the robotic arm may be controlled by generating and applying one or more joint space virtual fixtures, which are applied on a joint-by-joint level across one or more joints of the robotic arm. Similar to the task space virtual fixture described above, the joint space virtual fixture may be, for example, a straight or curved line, planar or curved surface, volume, or other construct in three-dimensional space (e.g., defined in Cartesian space or other suitable spatial coordinates). For example, the control system may generally limit motion of one or more control points on the robotic arm (e.g., any suitable virtual point on the robotic arm) to locations on or within the virtual fixture. Like the task space virtual fixture described above, the joint space virtual fixture may be predetermined (e.g., a precalculated or predefined location in space that is stored in memory and received for use during pre-operative and/or post-operative processes). For example, a particular joint space virtual fixture may be a general virtual fixture suitable for a varied range of situations, or may be associated with a particular surgery type, a particular patient type, a particular user (e.g., based on surgeon preferences), particular equipment such as type of patient table, etc. In some variations, the joint space virtual fixture may be stored in memory (e.g., relative to a current position of one or more links of the robotic arm) for use during a pre-operative, intra-operative, and/or post-operative process.

In some variations, at least one joint space virtual fixture may be defined on or around a joint of the robotic arm. Furthermore, multiple joint space virtual fixtures may be defined on or around multiple respective joints of the robotic arm, such that the movement of the robotic arm is substantially constrained to a reference plane or other virtual construct. For example, a user may manually manipulate and position the robotic arm with the actuated assistance provided by gravity compensation and/or friction compensation control modes. The joint space virtual fixtures may generally permit motion of the robotic arm within the reference plane, while substantially preventing or discouraging motion outside of the reference plane.

Different kinds of joint space virtual fixtures are possible. One variation of a joint space virtual fixture is illustrated in FIG. 3B. FIG. 3B illustrates ranges of rotational motion of a roll joint (e.g., roll joints J2, J4, J6 as shown in the exemplary robotic arm of FIG. 2A). A virtual fixture may be established at the target rotational angle 350 (e.g., which may be aligned with the reference plane). The control system may define an attraction region between angles (A) and (B) and around the target rotational angle 350. When the relative rotational positions of adjacent links enters the attraction region (AB) via a roll joint, a virtual force (e.g., a virtual spring force and/or virtual damping force similar to Equation 1 above) may attract the relative rotational positions toward the target rotational angle 350. The virtual forces may be used to determine one or more attractive joint torques that may be effected or imposed by actuation of the joint modules in the robotic arm, such that relevant joints of the robotic arm are driven to attract the arm links into particular target rotational angles, and thus encourage the robotic arm into a particular pose (e.g., within a reference plane). For example, in some variations, attractive joint torque to be applied by a joint module on a particular joint may be determined using Equation 3:

$$\tau = k^* \Delta\theta + d^* v_e \quad (3)$$

where $\tau$=joint torque, k=spring constant, $\Delta\theta$=penetration angle, d=damping ratio, and $v_\theta$=joint velocity.

The attraction region (AB) may, for example, allow a user manipulating a roll joint to feel the adjacent links "snap" or "lock" into a particular relative rotational position in accordance with the joint space virtual fixture. The attraction region (AB) may, in some variations, sweep an angle between about 10 degrees and about 50 degrees, between about 25 degrees and 35 degrees, or about 10 degrees. The attraction region (AB) may be symmetrically oriented around the target rotational angle 350 such that the target rotational angle 350 substantially bisects the attraction region (AB). Alternatively, the attraction region (AB) may be asymmetrically oriented around the target rotational angle 350, such that the target rotational angle 350 is closer to one end of the attraction region than the other.

In some variations, the robotic arm may be moved outside of the attraction region if sufficient external force applied to the robotic arm exceeds a threshold value. For example, the virtual forces may saturate at threshold values, or have maximum predetermined values, such that if a user attempts to rotate the robotic arm with enough force to overcome the maximum virtual forces, the roll joint may be forced outside of the attraction region. Outside of the attraction region (AB), the control system may refrain from applying virtual forces and attractive joint torques described above.

Figure 3C:
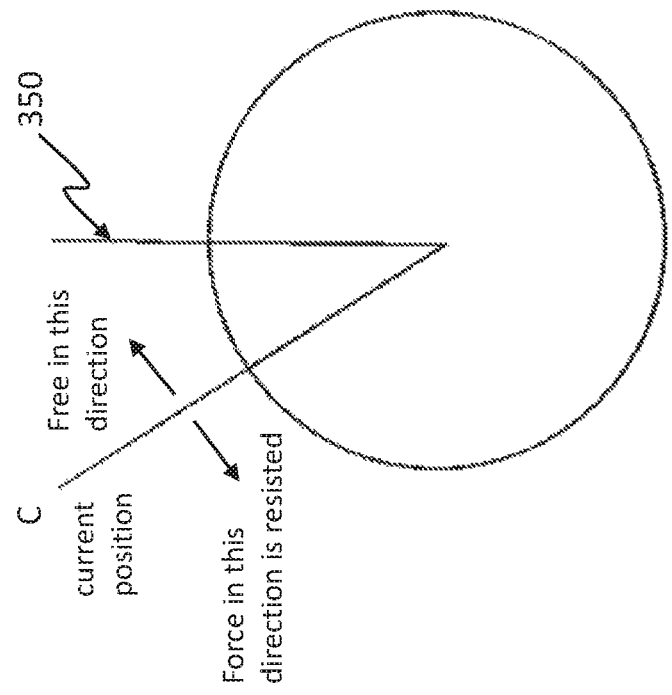
FIGS. 3B and 3C are schematic illustrations of exemplary variations of joint space virtual fixtures for controlling a robotic arm on a joint level.
Figure 3B:
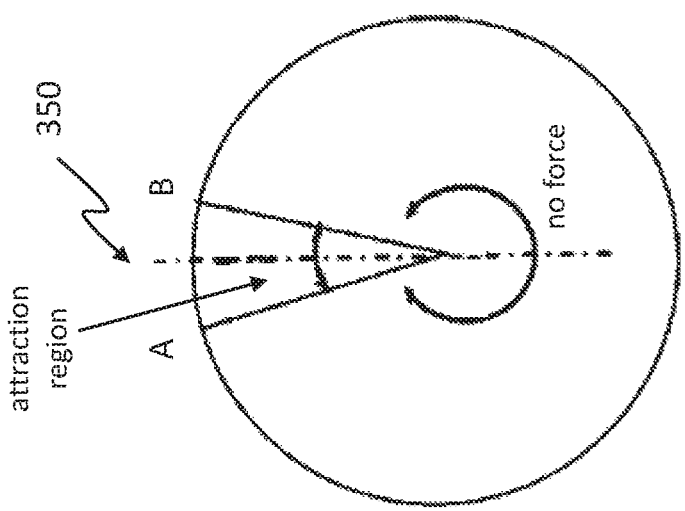

Another variation of a joint space virtual fixture is illustrated in FIG. 3C. Like FIG. 3B, FIG. 3C illustrates ranges of rotational motion of a roll joint, and a virtual fixture may be established relative to the target rotational angle 350 (e.g., which may be aligned with a reference plane). The control system may define a "one-sided" or unilateral virtual fixture that permits rotation of the joint in one direction toward the target rotational angle 350, but substantially prevents rotation of the joint in the opposite direction away from the target rotational angle 350 by actively opposing the movement. The control system may cause actuation of one or more joints to prevent rotation in accordance with the unilateral joint space virtual fixture. In some variations, the permissive direction of the unilateral virtual fixture may always be oriented in the same direction (e.g., permit only a clockwise movement of one link relative to an adjacent link). In other variations, the permissive direction of the unilateral virtual fixture may vary depending which direction of movement will more quickly position adjacent links at the target rotational angle 350. For example, if a current link position C is closer to the target rotational angle 350 by traveling in a clockwise direction, then the unilateral virtual fixture may substantially permit only clockwise movement of the link. As another example, if a current link position is closer to the target rotational angle 350 by traveling in a counter-clockwise direction, then the unilateral virtual fixture may substantially permit only counter-clockwise motion. Furthermore, in some variations, movement in the permissive direction may be assisted via actuated assistance (e.g., friction compensation).

In some variations, the robotic arm may be moved opposite the permissive direction of the unilateral virtual fixture if sufficient external force applied to the robotic arm exceeds a threshold value. For example, if a user attempts to rotate the robotic arm with enough force to overcome the threshold, the roll joint may be forced in the direction opposite the direction of the unilateral virtual fixture.

In some variations, multiple virtual fixtures may be combined in any suitable manner. For example, in one variation, the control system may be configured to implement, on at least one joint, either a "one-sided" unilateral virtual fixture (e.g., similar to that described above with respect to FIG. 3C) or a "two-sided" virtual fixture with an attraction region (e.g., similar to that described above with respect to FIG. 3B), depending on the current rotational position of a joint relative to a target rotational angle.

For example, as shown in FIG. 10A, if the difference between a current joint position $q_{curr}$ and a target joint position $q_{tar}$ is greater than a predetermined threshold $q_{threshold}$ (e.g., more than 5 degrees, more than 10 degrees, more than 15 degrees, etc.), then a one-sided, unilateral virtual fixture may be implemented. The unilateral virtual fixture may apply a virtual fixture force $F_v$ to restrict or oppose movement only if the difference between the current joint position $q_{curr}$ and a previous joint position $q_{prev}$ indicates that the joint is moving away from the target joint position $q_{tar}$. For example, as shown in FIG. 10A at box 1010, when the user is moving the arm toward the target position $q_{tar}$ (in a permissive direction of the unilateral virtual fixture, as determined at least in part on the difference between the current joint position $q_{curr}$ and a previous joint position $q_{prev}$), the control system may provide actuated assistance (e.g., friction compensation) with an assistive force $F_{ass}$ that is greater than zero to assist the arm movement toward the target position, and the unilateral virtual fixture may apply no virtual fixture force $F_v$ to restrict or oppose such arm movement. Conversely, as shown in FIG. 10A at box 1020, when the user is moving the arm away the target position $q_{tar}$ (in a restrictive direction of the unilateral virtual fixture, as determined at least in part on the difference between the current joint position $q_{curr}$ and a previous joint position $q_{prev}$), the control system may provide no actuated assistance with an assistive force $F_{ass}$ equal to about zero, and the unilateral virtual fixture may apply a virtual fixture force $F_v$ to substantially prevent or resist the arm movement away from the target position. Thus, the unilateral virtual fixture may facilitate joint motion toward a target joint position, and oppose joint motion away from the target joint position.

Furthermore, as shown in FIG. 10B, if the difference between a current joint position $q_{curr}$ and a target joint position $q_{tar}$ is less than a predetermined threshold $q_{threshold}$ (e.g., less than 5 degrees, less than 10 degrees, less than 15 degrees, etc.), then a "two-sided" virtual fixture with an attraction region may be implemented. For example, the control system may define an attraction region within a predetermined angular range around the target joint position $q_{tar}$. In some variations, the attraction region may also be defined as between the predetermined threshold $q_{threshold}$ on both sides of the target joint position, though the attraction region may be defined relative to any suitable angular range. When the relative rotational positions of adjacent links around a joint enters the attraction region, a virtual fixture force (e.g., a virtual spring force and/or virtual damping force similar to Equation 3 above) may attract the links to the target joint position. Accordingly, the two-sided virtual fixture may enable the adjacent links to "snap" or "lock" into a particular relative rotational position in accordance with the joint space virtual fixture, if the joint is pushed or pulled away a bit (e.g., within $q_{threshold}$ in either direction). In some variations, if, at any point, the difference between the current joint position $q_{curr}$ and a target joint position $q_{tar}$ becomes again more than a predetermined threshold $q_{threshold}$, then the control system may revert to implementing a one-sided virtual fixture as shown in FIG. 10A.

Furthermore, it should be understood that in some variations, a combination of the "one-sided" and "two-sided" virtual fixtures may be similarly implemented by the control system with task-based virtual fixtures described in further detail above. For example, a unilateral virtual fixture and/or a two-sided virtual fixture with an attraction region may be defined relative to a reference plane similar to that described above, and/or any suitable kind of virtual fixture shape.

Although the joint space virtual fixtures are primarily described with respect to roll joints, it should be understood that an attractive virtual fixture and/or unilateral virtual fixture may additionally or alternatively be similarly implemented for other kinds of joints in the robotic (e.g., pitch, yaw) to impose joint space guidance on other suitable portions of the robotic arm.

Different kinds of joint space virtual fixtures may be combined. For example, in some variations, a joint between adjacent links in the robotic arm may be primarily guided via a unilateral virtual fixture as described with respect to FIG. 3C, and when the relative rotational position of the links approaches the target rotational angle 350, it may enter an attractive region such that described with respect to FIG. 3B such that an attractive force snaps or locks the joint in place at the target rotational angle 350. Furthermore, in some variations, guidance via task space virtual fixture may be combined with guidance via one or more kinds of joint space virtual fixtures.

Guidance with Trajectories

In yet other variations, movement of at least a portion of the robotic arm may be guided in a trajectory following mode. In the trajectory following mode, the robotic arm may move to follow a sequence of one or more trajectory (e.g., Cartesian trajectory) commands. Trajectory commands may include, for example, velocity commands (framed in terms of linear and/or angular movement) or target pose commands (framed in terms of end objective position and orientation of the links and joint modules. If the command is a target pose that requires a number of link movements to transition from a current pose to the target pose, then the control system may generate a trajectory defining the necessary link movement. If the command relates to a target pose that is the same as the current pose, then the control system may generate trajectory commands effectively resulting in a commanded "hold" position. For instance, the trajectory may be based on inputs including: commanded velocities or poses (e.g., transformation matrix, rotation matrix, 3D vector, 6D vector, etc.), the arm links to be controlled, measured joint parameters (angles, velocities, accelerations, etc.), tool parameters (type, weight, size, etc.), and environmental parameters (e.g., predefined regions which the arm link is barred or forbidden from entering, etc.). The control system may then use one or more algorithms to generate the outputs of commanded joint parameters (position, velocity, acceleration, etc.) to the firmware and/or commanded motor currents as current feedforward to the firmware. Suitable algorithms for determining these output commands include algorithms based on forward kinematics, inverse kinematics, inverse dynamics, and/or collision avoidance (e.g., collision between arm links, between different instances of the robotic arm, between the arm and environment, etc.).

Pre-Operative Workflow

Figure 4A:
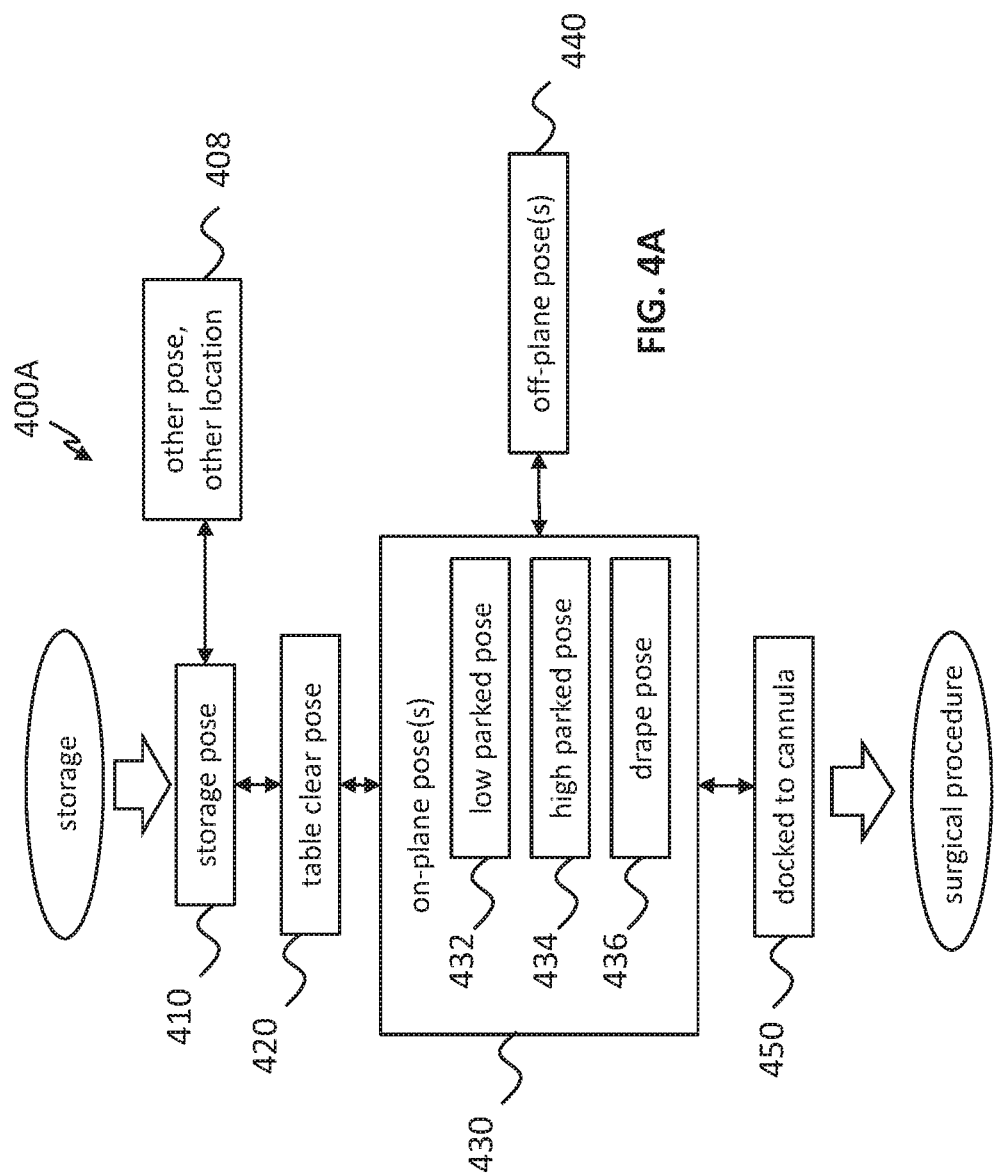
FIG. 4A is a flowchart of an exemplary workflow before a surgical procedure for a robotic surgical system.

In some variations, as described above, the method 300 may be used to help set up a robotic surgical system prior to a surgical procedure (e.g., to transition the robotic arm from a storage pose, another suitable starting pose, or otherwise prepare for use during a surgical procedure). Aspects of an exemplary variation of a method 400 in a pre-operative workflow setting are shown in FIG. 4A. For example, the method 400 may include assisting the robotic arm to move from a storage location (where the robotic arm may be in a storage pose such as a folded storage pose 410 as described below) to the reference location (where the robotic arm may be in a table clear pose 420 as described below, or another suitable pose in a location that sufficiently reduces the risk of colliding with nearby objects when the robotic arm unfolds from the folded storage pose 410). To further set up the robotic surgical system, at least one of the joints in the robotic arm may be driven to guide the robotic arm through a series of unfolded predetermined poses or poses within a reference plane defined at the reference location. The robotic arm may be guided among such on-plane poses 430 (e.g., low parked pose, high parked pose, drape pose), and subsequently to a docking position 450 for coupling to a cannula (e.g., a cannula placed in a port on a patient), via guidance with task space virtual fixtures, guidance with joint space virtual fixtures, guidance with trajectories, etc. The robotic arm may furthermore be moved outside of the reference plane, such as into one or more off-plane poses 440, and be guided back toward one or more on-plane poses 430 and/or to a docking position 450. Once in the docking position 450, the robotic arm may be positioned for receiving a surgical instrument (e.g., end effector to be driven by an instrument driver on the robotic arm) and/or otherwise prepared for use during a surgical procedure.

Storage Pose

In some variations, as shown in FIG. 4A, the method may include assisting the robotic arm to move from a storage pose 410. The storage pose 410 may be used, for example, to position the robotic arm when the robotic surgical system is not in use (e.g., between surgical procedures) and/or for transport of the robotic surgical system during shipping, between operating rooms, etc. Generally, when in the storage pose 410, the robotic arm may be in a compact pose and located in a suitable storage location, such as underneath or adjacent a patient table. The compact pose and/or storage location for the storage pose 410 may be predetermined and associated with a storage mode or state for the robotic arm, as stored in a memory device and received for use during pre-operative and/or post-operative processes for the robotic arm. In some variations, in the event that the robotic arm is in a different pose 408 not in the designated storage pose and/or storage location at the beginning of setup, the robotic system may indicate an error to the user that the robotic arm is not in the storage pose 460 and/or move or otherwise guide the robotic arm to the storage pose 460.

As shown, for example, in FIGS. 5A and 5B, the compact pose may generally be a folded pose in which the links of the robotic arm 200 are efficiently packed against each other so as to enable the robotic arm to occupy minimal volume. For example, as shown in FIG. 5B, the robotic arm 200 may include a first portion 200a and a second portion 200b which are movable relative to each other (e.g., pivotably coupled), and when the robotic arm 200 is in the storage pose, the second portion 200b may be collapsed onto or nested adjacent to the first portion 200a. Additional portions of the robotic arm 200, such as portions more distal than the second portion 200b, may similarly be collapsed onto or nested adjacent to more proximal portions of the robotic arm. In some variations, when in the storage pose 410, the robotic arm 200 may be in compact pose underneath the patient table in a designated storage location. In variations in which the robotic surgical system includes multiple robotic arms, the multiple robotic arms may be generally arranged in their storage poses in a symmetrical manner underneath or around the patient table (or may be arranged in any suitable manner).

When the robotic arm 200 is in the storage pose 410, at least a portion of the robotic arm may be locked in the storage pose 410, such as via engagement of one or more brakes in at least on joint in the robotic arm. For example, all of the brakes in the robotic arm (and/or coupling arrangement coupling the robotic arm to the table) may be engaged to hold the robotic arm in the storage pose 410 until the robotic arm is ready to transition to a predetermined reference location.

Although FIGS. 5A and 5B illustrate a storage pose that is generally under a patient table, it should be understood that in some variations, the storage pose may be inside a cart, under or above a ceiling, adjacent or inside a side wall, or folded against any other suitable mounting surface. For example, the arm may be in a folded pose similar to that illustrated in FIGS. 5A and 5B, located within a storage compartment (e.g., folded within a cart, within a ceiling, within a sidewall) or nestled against a support surface (e.g., folded against a cart, ceiling, or side wall).

Table Clear Pose

As shown in FIG. 4A, the robotic arm may transition from the storage pose 410 to a table clear pose 420, or another suitable pose in a reference location suitable for allowing the robotic arm to unfold without colliding with the table and/or other nearby objects. For example, as shown in FIGS. 6A and 6B, at least a first portion 200a of the robotic arm may pivot outward from the table 250 in order to enable a second portion 200b of the robotic arm to be clear of the table 250 for unfolding, etc. For example, with reference to FIG. 2, when the robotic arm is transitioning to the table clear pose, the links L0 and L1 may pivot outward around via pin 252 relative to the table 250, such that more distal links of the robotic arm (e.g., L2-L7 and other distal portions of the robotic arm) may unfold and/or otherwise reconfigure without colliding with the table. One or more brakes in the robotic arm and/or coupling arrangement may be disengaged to facilitate such movement of the robotic arm from the storage pose 410 to the reference location.

In some variations, the reference location for the table clear pose 420 may be described as an angle (or range of angles) of at least a designated portion of the robotic arm relative to the patient table. For example, with reference to FIG. 6B, the reference location may be defined at least in part by an angle $\alpha$ as measured between a proximal portion 200a of the robotic arm and an edge of the patient table 250. The angle $\alpha$ may be, for example, at least 45 degrees, at least 60 degrees, at least 75 degrees, or at least 90 degrees. In other exemplary variations, the angle $\alpha$ may be between about 30 degrees and about 90 degrees, between about 45 degrees and about 75 degrees. In yet other variations, the reference location may be any suitable angle that positions the robotic arm out from under the patient table 250 and allows the arm to unfold, which may depend at least partially on, for example, the robotic arm design (e.g., length or diameter of arm links, number of arm links, etc.).

It should be understood that in other variations, other kinds of mechanisms may additional or alternatively enable the robotic arm to transition to the table clear pose in some manners, such as through longitudinal translation (e.g., sliding on a longitudinal track) ad/or lateral translation (e.g., sliding on a lateral track), in addition to or as an alternative to pivoting.

In some variations, the robotic arm may be guided to the reference location in response to a movement command (e.g., via a remote command from a handheld communication device or other interface), such as through a trajectory following mode. In some variations, the robotic arm may be guided to the reference location with user manipulation of the robotic arm (e.g., with gravity compensation and/or friction compensation), guidance with one or more task space virtual fixtures, and/or guidance with one or more joint space virtual fixtures.

A reference plane may be defined at the predetermined reference location for the robotic arm. In some variations, the reference plane may be defined as a plane generally perpendicular to a proximal portion of the robotic arm. For example, with reference to FIG. 2A, the reference plane may be a vertical plane orthogonal to the robotic arm link L1. Once the robotic arm has transitioned to the table clear pose 420, the robotic arm may be guided to prepare for unfolding and/or other repositioning within the reference plane. For example, as shown in FIG. 6C, the robotic arm 200 (still in a generally folded or collapsed pose) may roll such that both the first arm portion 200a and the second arm portion 200b lie on a reference plane 610. After the robotic arm 200 rolls onto the reference plane 610, the robotic arm 200 may reconfigure itself through various folded and unfolded poses within the reference plane 610, as further described below (e.g., low parked pose, high parked pose, drape pose).

In some variations, only a first portion 200a may rotate to cause the robotic arm 200 to roll onto the reference plane, while the second portion 200b and other portions of the robotic arm remain in the same orientation relative to the first portion 200a. In other variations, other portions of the robotic arm may additionally move while the robotic arm 200 rolls onto the reference plane. For example, the second portion 200b may include a touchscreen, display, buttons, and/or other user interface elements (not shown) that are ideally easily accessible to the user throughout setup of the system. When the robotic arm 200 is in the table clear pose (e.g., as shown in FIG. 6B), the second portion 200b may be oriented such that the user interface elements are upward-facing and accessible to a user. As the first portion 200a rotates in a clockwise direction as shown in FIG. 6C, the second portion 200b may additionally rotate in a counter-clockwise direction at the same or similar rate, in order to keep the user interface elements upward-facing throughout the robotic arm's transition onto the reference plane.

Although the robotic arm's transition between the storage pose (e.g., FIGS. 5A and 5B) and an initial on-plane pose (e.g., FIG. 6C) is primarily described above as a process with the table clear pose (e.g., FIGS. 6A and 6B) as a discrete, intermediate step, it should be understood that in some variations, the transition between the storage pose may omit such a discrete intermediate pose. For example, in some variations, the robotic arm may substantially simultaneously pivot outwards and roll onto the reference plane, thereby blending together the movements described above with respect to transitioning between the storage pose and the table clear pose, and between the table clear pose and the initial on-plane pose. Even further, in some variations, the robotic arm may substantially simultaneously pivot outwards and roll onto the reference plane into one of the on-plane poses described below, thereby omitting the initial on-plane pose shown in FIG. 6C.

On-Plane Poses

In some variations, as shown in FIG. 4A, once the robotic arm has been positioned within a reference plane situated at the reference location, the robotic arm may be guided through a series of on-plane poses 430, or one or more poses substantially constrained within the reference plane. For example, in some variations, a pose substantially constrained within the reference plane may be a pose in which the robotic arm (or selected key locations or points on the robotic arm) lie within the reference plane. One or more brakes in the robotic arm may be disengaged to permit repose of the robotic arm. Such brake disengagement may be triggered, for example, upon the application of an external force (such as a user beginning to manually manipulate the robotic arm, and/or engagement of a button, mechanism, or other surface on a control point on the robotic arm).

Figure 7B:
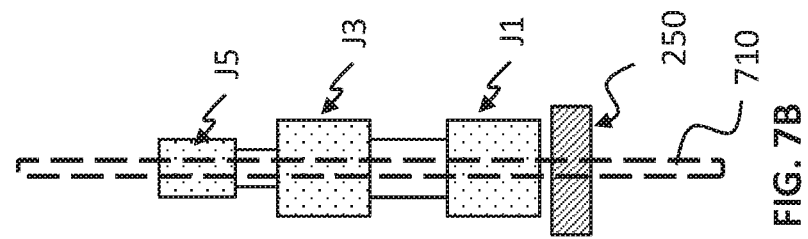
FIGS. 7A and 7B are illustrative schematic side views of a robotic arm movable to different poses within an exemplary reference plane.
Figure 7A:
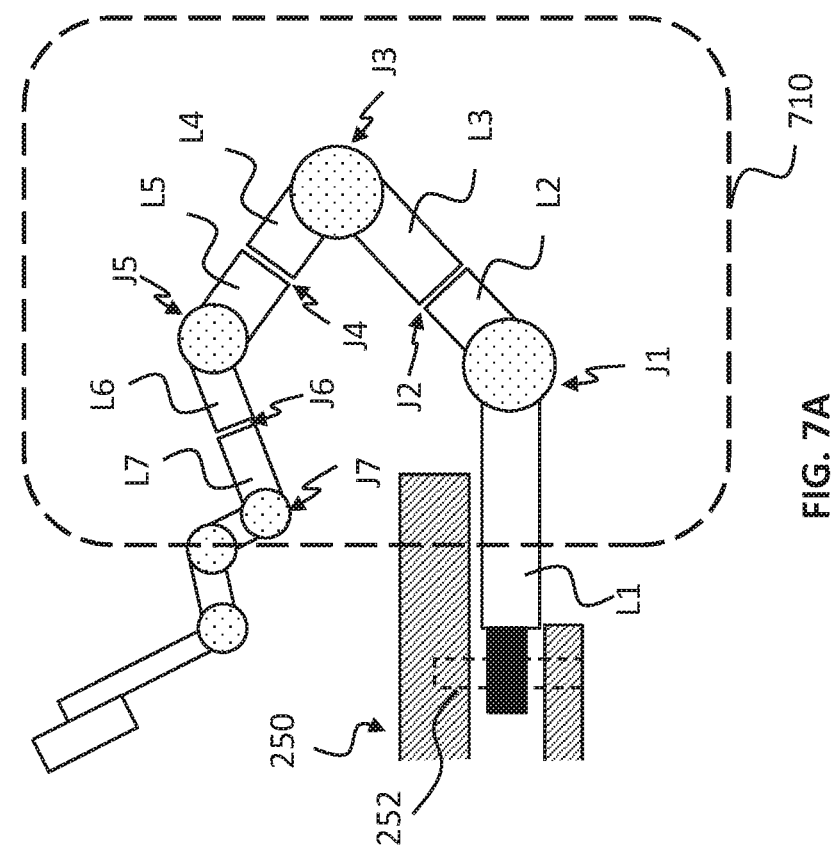

For example, FIGS. 7A and 7B illustrate one pose of the robotic arm substantially constrained within a reference plane 710. The robotic arm pictured in FIGS. 7A and 7B may be substantially similar to that shown in FIG. 2A. Generally, the angle or orientation of the reference plane may be defined or set based on a particular rotational angle of the roll joints J2, J4, and/or J6. Movement of any of the roll joints J2, J4, and J6 facilitates out-of-plane movement of the robotic arm (or alternatively, cause a change in angle or orientation of the plane that is shared among the roll joints). Furthermore, the pivot joints J1, J3, J5, and J7 lie on the reference plane 710, and movement of the joints J1, J3, J5, and/or J7 facilitates different on-plane poses of the robotic arm.

In a pre-procedural setup process, the series of poses substantially constrained within the reference plane may, for example, include an ordered sequence of progressively unfolded predetermined poses that are within the reference plane. In some variations, one or more of the joints in the robotic arm may be actuated to drive the robotic arm both forward and backward through at least a portion of the ordered sequence. For example, the robotic arm may be driven to unfold partially, refold at least partially, then unfold fully through the sequence of poses. By substantially constraining the robotic arm within a reference plane during pre-operative procedures such as unfolding, unexpected collisions between the robotic arm and nearby objects (as well as self-collision) may be reduced. Positioning the robotic arm into predetermined poses may further limit the risk of collisions, since the robotic arm will move in predictable and consistent ways as it is prepared for surgical procedures.

In some variations, collisions such as self-collision among the robotic arm's links may be reduced by introducing joint limits. For example, one or more of the joints in the robotic arm may be restricted to movement within a particular range of motion, such that in combination, multiple joints are not able to rotate to the extent that would cause arm links to collide. The joint limits may be "soft" in that a joint limit may be overcome by applying (e.g., manually) a force to the joint that exceeds a threshold force. In some variations, such joint limits may be imposed with virtual fixtures, similar to the joint space fixtures described above.

As shown in FIG. 4A, some exemplary on-plane poses 430 include a low parked pose 432, a high parked pose 434, and a drape pose 436. As shown in FIG. 8A, the robotic arm in a low parked pose 432 may be partially unfolded, with at least some of the robotic arm positioned below the patient table 250. The low parked pose 432 may, for example, be useful to keep the robotic arm in an intermediate pose that is out of storage, but in a known position that is out of the way as other robotic arms are being manipulated or as personnel (e.g., surgical assistants) become oriented around the patient table, etc.

As shown in FIG. 8B, the robotic arm in a high parked pose 434 may be more unfolded than the low parked pose 432, but include a distal portion that is folded and compact. In the high parked pose 434, the robotic arm may be in an intermediate position between the table clear pose 420 and the drape pose 436. The high parked pose 434 may be another intermediate pose that is out of storage but is in a known position that is out of the way.

As shown in FIG. 8C, the robotic arm in a drape pose 436 may be even more unfolded than the high parked pose 434. For example, as shown in FIG. 8D, in the drape pose 436, the robotic arm may be sufficiently unfolded so as to enable placement of a sterile drape 820 collectively around the arm links in a manner that allows articulation of the arm links underneath the sterile drape 820. For example, after a user moves the robotic arm into the drape pose 436, the robotic arm may hold the drape pose with the assistance of gravity compensation while the user places the sterile drape over the robotic arm. In some variations of a clinical workflow, the patient may be draped when the robotic arm is in the drape pose (e.g., immediately before or immediately after the robotic arm is covered in the sterile drape).

In some variations, the ordered sequence of progressively unfolded predetermined poses includes the low parked pose 432, the high parked pose 434, and the drape pose 436. Other variations of ordered sequences may omit one or more of these poses, and/or include other suitable poses (e.g., poses that are generally intermediate between any two of these poses, modified versions of these poses, etc.).

Movement among the predetermined poses may be guided by automatic driving of at least one of the plurality of joints in the robotic arm. Various guidance processes may guide the robotic arm through the poses. For example, one or more joints may be driven to facilitate gravity compensation and/or friction compensation to help guide movement of the robotic arm in response to user-applied forces on the robotic arm as the user manually manipulates the robotic arm. Additionally or alternatively, one or more joints may be driven to guide the robotic arm through movements according to one or more task space virtual fixtures and/or one or more joint space virtual fixtures.

When enforcing one or more joint space virtual fixtures, different joints may be actuated in a particular order to effectively move the robotic arm through the ordered sequence of progressively unfolded poses (e.g., for avoidance of self-collision between its own arm links, to sweep less volume as the robotic arm unfolds, etc.). For example, in some variations, more proximal joints may be biased to unfold before more distal joints in the robotic arm, so as to reduce the overall volume that the robotic arm sweeps during the sequence of unfolding poses. With respect to the exemplary variation of the robotic arm shown in FIG. 2A, to guide the robotic arm through the various on-plane poses, the method may including a first joint space virtual fixture on J2, a second joint space virtual fixture on J4, and a third joint space virtual fixture on J6, where the first, second, and third joint space virtual fixtures are enforced in that order.

Figure 9:
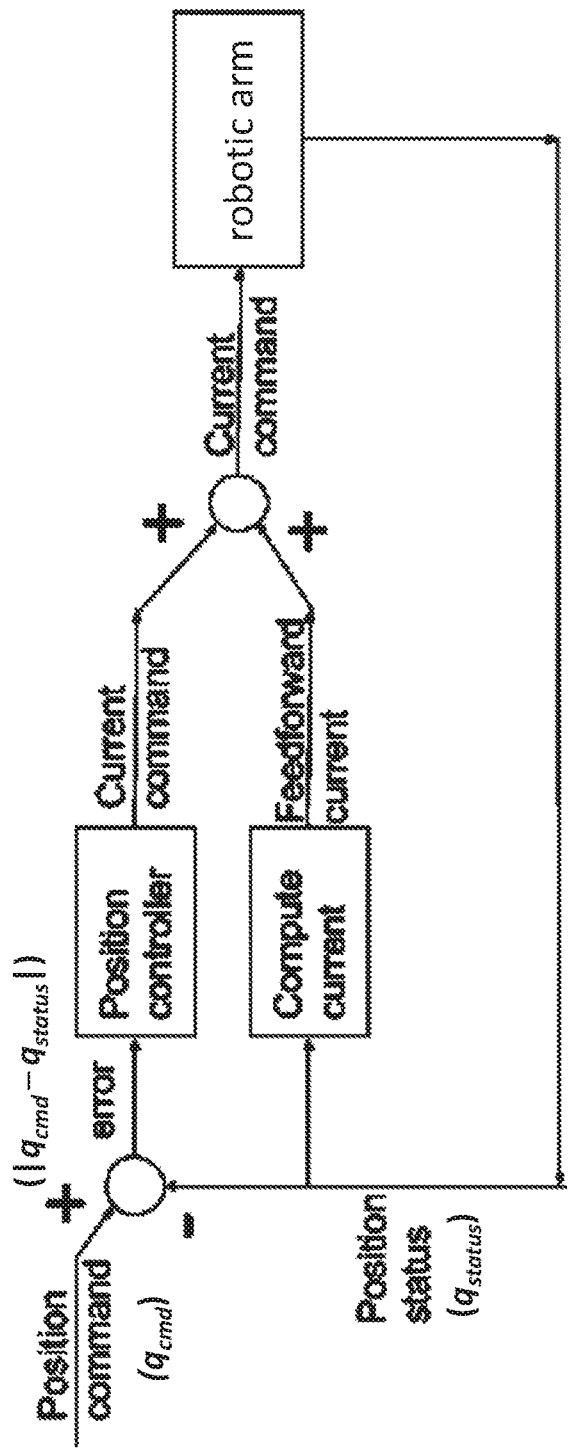
FIG. 9 is a diagram illustrating an exemplary variation of a control system implementing a trajectory following mode for a robotic arm.

In some variations, one or more joints of the robotic arm may be driven to facilitate an automatic trajectory following mode in which the robotic arm follows predetermined, prescribed movement commands. For example, an unfolding trajectory may be precalculated on a joint level for the robotic arm, for commanding each of the joints (e.g., J1-J7 with reference to the robotic arm variation shown in FIG. 2A) to gradually transition the robotic arm from the table clear pose 420 to an on-plane pose 430. In some variations, the control system overseeing execution of the trajectory may follow a set of rules illustrated in FIG. 9. Generally, when executing a commanded trajectory $q_{cmd}$, the joint position controllers may have soft gains and may be compensated by pre-calculated joint torques in a feedforward manner. As the trajectory following mode is active, the actual position of the joints may be detected with sensors in the robotic arm (e.g., with encoders) and utilized in the control system as $q_{status}$. The feedforward terms contributing to the pre-calculated joint torques may include joint torques calculated for effecting movement of the joints and joint torques required for gravity compensation (as described above). The soft gains on the joints and the feedforward gravity terms may allow the robotic arm to follow the predetermined trajectory, yet comply with unexpected external forces (e.g., due to collisions with nearby objects, interference among its own links, etc.). For example, detectable tracking error ($|q_{cmd}-q_{status}|$) may indicate when the robotic arm is obstructed due to collision, etc. and the soft gains will prevent potentially dangerous buildup of commanded torques in the robotic arm. Furthermore, in some variations, if tracking error ($|q_{cmd}-q_{status}|$) exceeds a particular threshold, then the trajectory following mode may be paused or abandoned (i.e., to stop the execution of the trajectory).

One guidance process may be used for moving the robotic arm throughout the entire series of predetermined poses. Alternatively, different guidance processes may be used for different portions of the series of predetermined poses. For example, a trajectory following mode may guide the robotic arm from the table clear pose to an initial on-plane pose, a task space or joint space virtual fixture may guide the robotic arm between the initial on-plane pose and the low parked pose, and only gravity and friction compensation modes may guide the robotic arm between the high parked pose and the drape pose). Other combinations and permutations of guidance processes throughout setup may be possible in other variations. For example, the system may be set to operate based on user particular preferences for trajectory following, task space or joint space virtual fixtures, or manual manipulation with gravity and/or friction compensation. Such user preference for a particular guidance process may apply for the entire series of poses, or for transitions between particular poses. As another example, the system may be set to operate based on patient-specific, procedure-specific, equipment-specific, and/or room-specific parameters. For example, different patients (e.g., different patient sizes), different personnel, different surgical procedures, or different operating room environments may establish different spatial constraints or other constraints that may make certain kinds of guidance processes more suitable than others. As an illustrative example only, a bedside assistant may be too short to manually manipulate the robotic arm throughout all poses with gravity and friction compensation, so in such instances a trajectory following mode may be more appropriate.

In some variations, a virtual fixture (e.g., providing a soft spring force and/or damping force) and/or brakes may help maintain the pose of at least some of the links while the rest of the links in the robotic arm move. For example, a transition from the low parked pose to the high parked pose (or another initial on-plane pose after the table clear pose to high park pose) may involve a virtual fixture and/or brakes to substantially arrest relative movement between distal links of the robotic arm, which may help maintain a folded pose of the distal links as a user pulls on the robotic arm to unfold the robotic arm between the low parked pose to the high parked pose. For example, with reference to the exemplary robotic arm shown in FIG. 2A, when a user is pulling or otherwise manipulating the robotic arm into the high parked pose, joints J6 and J7 near the distal portion of the robotic may be locked together to keep adjacent links in a folded pose.

As shown in FIG. 4A, the robotic arm may furthermore selectively move into off-plane poses 440, or poses that are not in the reference plane. For example, the robotic arm may move from an on-plane pose 430 to an off-plane pose 440 (e.g., by breaking free of a virtual fixture with sufficient force). An off-plane pose may be desirable in, for example, emergency scenarios in which the robotic arm must be moved quickly out of the way to provide immediate bedside access to the patient. Additionally or alternatively, the off-plane pose(s) 430 may be achieved by the robotic arm moving from any position, including the table clear pose 420. In some variations, movement of the robotic arm to and from an off-plane pose may be guided in a manner substantially similar to movement among on-plane poses described above. For example, a task space virtual fixture and/or joint space virtual fixture may help bias the robotic arm back toward the reference plane (e.g., a low parked pose 432, a high parked pose 434, a drape pose 436, or another suitable on-plane pose 430).

Docking

Once the robotic arm is draped with a sterile drape, the robotic arm may be moved to a pose 450 for docking to a cannula that is placed in the patient to provide a passageway through which a surgical instrument may be inserted into the patient. For example, the robotic arm may be moved (e.g., manipulated manually by a user under gravity compensation and/or friction compensation) such that the distal end of the robotic arm is closer to a placed cannula. An instrument driver, disposed on the distal end of the robotic arm, may couple to the cannula such that the robotic arm is in the pose 450 docked to the cannula. The docked pose 450 may, for example, indicate that the robotic arm is prepared for use during a surgical procedure using a surgical instrument associated with the robotic arm (e.g., coupled to the instrument driver and passing through the cannula into the patient).

Post-Operative Workflow

In some variations, as described above, the method 300 may be used to help "teardown" a robotic surgical system after a surgical procedure. Aspects of an exemplary variation of the method in a post-operative workflow setting are shown in FIG. 4B. Generally, the post-operative workflow summarized in FIG. 4B may be similar to the pre-operative workflow summarized in FIG. 4C, except the post-operative workflow may include processes in reverse order compared to the pre-operative workflow.

Undocking

After a surgical procedure (or in other circumstances in which a robotic arm is to be removed from a patient site), a robotic arm may be decoupled from the cannula and moved into an undocked pose 460. The undocked pose 460 may be any suitable pose in which the robotic arm is moved away from the patient (e.g., outside of a predefined boundary around the patient, such as at least several feet away from the patient). The robotic arm may, for example, be manually manipulated by a user with the assistance of gravity compensation and/or friction compensation (or alternatively with trajectory following, etc.), away from the patient and into the undocked pose 460. In some variations, the undocked pose 460 may be an on-plane pose 430 (e.g., on a reference plane), though alternatively the undocked pose 460 may be any suitable pose that is not within the reference plane.

On-Plane Poses, Table Clear Pose

As shown in FIG. 4B, after being undocked from the cannula, the robotic arm may be moved toward an on-plane pose 430 that is on a reference plane. During a post-operative workflow, movement of the robotic arm toward and among on-plane poses 430 and/or other poses within a reference plane may, in some variations, be guided in one or more manners as described above for pre-operative workflow (e.g., guided with a task space virtual fixture and/or joint space virtual fixture, etc.).

When enforcing one or more joint space virtual fixtures, different joints may be actuated in a particular order to effectively move the robotic arm through the ordered sequence of progressively folded poses (e.g., for avoidance of self-collision between its own arm links, to sweep less volume as the robotic arm unfolds, etc.). For example, in some variations, more distal joints may be biased to fold before more proximal joints in the robotic arm, so as to reduce the overall volume that the robotic arm sweeps during the sequence of folding poses. With respect to the exemplary variation of the robotic arm shown in FIG. 2A, to guide the robotic arm through the various on-plane poses, the method may including a first joint space virtual fixture on J6, a second joint space virtual fixture on J4, and a third joint space virtual fixture on J2, where the first, second, and third joint space virtual fixtures are enforced in that order.

As another example, the robotic arm may be guided with external forces (e.g., user manipulations) toward a drape pose 436 where the sterile drape may be removed from the robotic arm. From the drape pose 436, the robotic arm may be guided toward the high parked pose 434 and/or the low parked pose 432. The robotic arm may subsequently be guided toward the table clear pose 420 (e.g., substantially folded into a compact pose) at the reference plane or reference location.

Furthermore, similar to that described for pre-operative workflow, in some variations, the robotic arm may be manipulated to one or more off-plane poses 440 not in the reference plane, and subsequently biased back toward the reference plane via a virtual fixture or the like.

Storage Pose

In some variations, as shown in FIG. 4B, the robotic arm may transition from the table clear pose 420 at the reference location or reference plane to the storage pose 410. In some variations, the robotic arm may be guided to the storage pose 410 in response to a movement command (e.g., via a remote command from a handheld communication device or other interface), such as through a trajectory following mode. In some variations, the robotic arm may be guided to the storage pose with user manipulation of the robotic arm (e.g., with gravity compensation and/or friction compensation), guidance with one or more task space virtual fixtures, and/or guidance with one or more joint space virtual fixtures. Similar to that described above, generally, when in the storage pose 410, the robotic arm may be in a compact pose (e.g., underneath or adjacent a patient table) associated with a storage mode or state for the robotic arm. In some variations, in the event that the robotic arm is in a different pose 408 not in the designated storage pose and/or storage location at the beginning of setup, the robotic system may indicate an error to the user that the robotic arm is not in the storage pose 460 and/or move or otherwise guide the robotic arm to the storage pose 460.

Example

In one exemplary variation, a proximal end of a robotic arm may be coupled, via a coupling arrangement, to a patient table on which a patient lies. The coupling arrangement may include an actuator to actuate a laterally pivoting joint, and one or more brakes to arrest movement of the lateral pivoting joint. In an exemplary pre-operative workflow, a robotic arm may begin in a storage pose located underneath the patient table, where the robotic arm may be in a folded, compact pose. Brakes in the robotic arm and brake in the coupling arrangement may be engaged to hold the storage pose of the robotic arm under the table. A trajectory following mode may be enabled, and a trajectory for moving the robotic arm from the storage pose to a table clear mode may be loaded from a memory device into a control system. The brake in the coupling arrangement may be disengaged, and the laterally pivoting joint may be actuated in accordance with the loaded trajectory such that the folded robotic arm laterally pivots to table clear pose at a reference location located at least 45 degrees laterally away from the patient table.

A user may pull and otherwise manually manipulate the robotic arm to unfold from the table clear pose to a pose located substantially on a reference plane at the reference location, where the reference plane is perpendicular to a proximal link of the robotic arm. Through these manual manipulations, one or more joints of the robotic arm may be driven to assist these motions with one or more actuators in accordance with a task space virtual fixture and/or a joint space virtual fixture, which may substantially guide or constrain movement of the robotic arm within the reference plane. When a user moves (e.g., pushes or pulls) the robotic arm, a friction compensation mode may be enabled to help the user overcome friction and enable the user to move the robotic arm more easily. Furthermore, when the user lets go of the robotic arm, the robotic arm may maintain its current pose due to actuation of one or more joints in gravity compensation mode. Generally, the user may manually move the robotic arm through various poses under guided motion within the reference plane including a high parked pose and a drape pose. When the robotic arm is in the drape pose, the robotic arm may be held stationary due to gravity compensation, and the user may cover at least a portion of the robotic arm with a sterile drape in order to isolate the non-sterile robotic arm from a sterile environment.

The draped robotic arm may be further manually manipulated by the user toward a cannula placed in a suitable location in the patient on the patient table, with the assistance of gravity compensation and friction compensation. For example, the user may pull an instrument driver (on the distal end of the robotic arm) toward a cannula that is inserted in a desired location in the patient, and couple (dock) the instrument driver and robotic arm to the cannula. In this docked position, the instrument driver is ready to receive a surgical instrument (e.g., endoscopic camera, end effector, etc.) that will pass through the cannula, and the robotic arm is prepared for use during a robotic surgical procedure.

Following completion of the robotic surgical procedure, an exemplary post-operative workflow includes similar steps as the pre-operative workflow performed substantially in reverse. The instrument driver may be decoupled (undocked) from the cannula, and the robotic arm is manually manipulated by the user away from the patient with the assistance of gravity compensation and friction compensation. The robotic arm may be moved far enough away from the patient to enter the same or similar reference plane as during the pre-operative workflow, and may be repositioned to various poses substantially constrained within the reference plane, including the drape pose. As before, when the robotic arm is in the drape pose, the robotic arm may be held stationary due to gravity compensation, and the user may remove the sterile drape from the robotic arm. Generally, the user may continue to manually move the robotic arm under guided motion to fold the robotic arm from the drape pose, to the high parked pose, and to the table clear pose (or close to it) in which the robotic arm is folded into a compact pose. Throughout these movements, one or more joints of the robotic arm may be driven to assist these motions one or more actuators in accordance with a task space virtual fixture and/or a joint space virtual fixture to substantially guide or constrain movement of the robotic arm within the reference plane.

From the table clear pose, the trajectory following mode may be enabled, and a trajectory for moving the robotic arm from the table clear pose to the storage pose may be loaded from the memory device into the control system. The laterally pivoting joint may be actuated to move the folded robotic arm from the table clear pose to the storage pose. Brakes in the coupling arrangement and within the robotic arm may be engaged to keep the robotic arm in the storage pose (e.g., until the robotic arm is to be prepared for another surgical procedure).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A method for controlling a robotic arm in a robotic surgical system, the method comprising:
    defining a reference plane at a predetermined reference location for the robotic arm, wherein the robotic arm comprises a plurality of joints; and
    driving at least one of the plurality of joints to guide the robotic arm through a series of predetermined poses substantially constrained within the reference plane including enforcing a joint space virtual fixture on the at least one of the plurality of joints, to bias the robotic arm toward the reference plane.

2. The method of claim 1, wherein the series of predetermined poses comprises an ordered sequence of progressively unfolded predetermined poses.

3. The method of claim 1, wherein the series of predetermined poses comprises an ordered sequence of progressively folded predetermined poses.

4. The method of claim 1, further comprising driving at least one of the plurality of joints to guide the robotic arm through the series of predetermined poses to transition from a storage pose.

5. The method of claim 4, further comprising driving at least one of the plurality of joints to guide the robotic arm through the series of predetermined poses to transition to the storage pose.

6. The method of claim 1, wherein driving at least one of the plurality of joints comprises enforcing a task space virtual fixture at the reference plane, to bias the robotic arm toward the reference plane.

7. The method of claim 1, wherein the joint space virtual fixture is uni-directional.

8. The method of claim 1, wherein driving at least one of the plurality of joints comprises generating a virtual attractive force at the at least one joint in the joint space virtual fixture, to bias the robotic arm toward the reference plane.

9. The method of claim 1, wherein the series of predetermined poses comprises an ordered sequence, and wherein driving at least one of the plurality of joints comprises driving at least one of the plurality of joints forward and backward through at least a portion of the ordered sequence.

10. The method of claim 1, wherein driving at least one of the plurality of joints comprises driving the at least one joint in response to an external force on the robotic arm.

11. The method of claim 10, wherein driving at least one of the plurality of joints comprises applying a gravity compensation torque to at least one of the plurality of joints.

12. The method of claim 10, wherein driving at least one of the plurality of joints comprises applying a friction compensation torque to at least one of the plurality of joints.

13. The method of claim 1, wherein driving at least one of the plurality of joints comprises driving the at least one joint according to a predetermined trajectory through the series of predetermined poses which includes folded and unfolded predetermined poses.

14. A robotic surgical system, comprising:
at least one robotic arm comprising a plurality of joints;
a processor configured to control movement of the at least one robotic arm by defining a reference plane at a predetermined reference location and driving at least one of the plurality of joints to guide the at least one robotic arm through a series of predetermined poses substantially constrained within the reference plane in accordance with a joint space virtual fixture, to bias the at least one robotic arm toward the reference plane.

15. The system of claim 14, wherein the series of predetermined poses comprises an ordered sequence of progressively unfolded predetermined poses.

16. The system of claim 14, wherein the series of predetermined poses comprises an ordered sequence of progressively folded predetermined poses.

17. The system of claim 14, wherein the processor is configured to drive at least one of the plurality of joints in accordance with a task space virtual fixture.

18. The system of claim 14, wherein the joint space virtual fixture is uni-directional.

19. The system of claim 14, wherein the processor is configured to drive the at least one joint in response to an external force on the at least one robotic arm.

20. The system of claim 14, wherein the processor is configured to drive the at least one joint according to a predetermined trajectory through the series of predetermined poses.

* * * * *